United States Patent
Yoshida et al.

(10) Patent No.: US 11,299,722 B2
(45) Date of Patent: Apr. 12, 2022

(54) MODIFIED LIPASE AND USE THEREOF

(71) Applicant: AMANO ENZYME INC., Nagoya (JP)

(72) Inventors: Kazunori Yoshida, Kakamigahara (JP); Tetsuya Takahashi, Kakamigahara (JP); Kazuhiko Ishikawa, Ikeda (JP)

(73) Assignee: AMANO ENZYME INC., Nagoya (JP)

( * ) Notice: Subject to any disclaimer, the term of this patent is extended or adjusted under 35 U.S.C. 154(b) by 0 days.

(21) Appl. No.: 16/639,871

(22) PCT Filed: Aug. 17, 2018

(86) PCT No.: PCT/JP2018/030463
§ 371 (c)(1),
(2) Date: Feb. 18, 2020

(87) PCT Pub. No.: WO2019/044531
PCT Pub. Date: Mar. 7, 2019

(65) Prior Publication Data
US 2020/0362322 A1    Nov. 19, 2020

(30) Foreign Application Priority Data
Sep. 1, 2017  (JP) .............................. JP2017-168995

(51) Int. Cl.
*C12N 9/20* (2006.01)
*C12P 7/64* (2006.01)

(52) U.S. Cl.
CPC . *C12N 9/20* (2013.01); *C12P 7/64* (2013.01)

(58) Field of Classification Search
CPC ...................................... C12N 9/20; C12P 7/64
See application file for complete search history.

(56) References Cited

U.S. PATENT DOCUMENTS 7,662,602 B2 *  2/2010  Yaver ..................... C12N 9/20
                                                435/193
2016/0319259 A1  11/2016  Ishigaki et al.

FOREIGN PATENT DOCUMENTS

| CN | 106085975 A | 11/2016 |
| EP | 3081644 B1 | 3/2019 |
| JP | S63-304992 A | 12/1988 |
| JP | 2003-144162 A | 5/2003 |
| JP | 2017-073980 A | 4/2017 |
| WO | 2012/077614 A1 | 6/2012 |

(Continued)

OTHER PUBLICATIONS

Benjamin. *Candida rugosa* lipases: molecular biology and versatility in biotechnology. Yeast 14:1069-1087 (1998).*

(Continued)

*Primary Examiner* — Yong D Pak
(74) *Attorney, Agent, or Firm* — Locke Lord LLP

(57) ABSTRACT

The present invention has an object of providing a modified lipase having excellent stability and reactivity at a high temperature. Provided is a modified lipase with improved reactivity and/or stability at a high temperature, the modified lipase having an amino acid sequence including one or more amino acid substitutions which are selected from the group consisting of T130C-S153C, A249P, F259Y, S282P, S283Y and S300P in the amino acid sequence represented by SEQ ID NO: 1, or an amino acid sequence having 90% or more sequence identity therewith.

13 Claims, 2 Drawing Sheets
Specification includes a Sequence Listing.

| | Relative activity | Ratio to wild type activity |
|---|---|---|
| Wild type | 5% | 1 |
| T130C-S153C | 29% | 5.8 |
| A249P | 9% | 1.8 |
| F259Y | 20% | 4.0 |
| S282P | 16% | 3.3 |
| S283Y | 27% | 5.4 |
| S300P | 22% | 4.4 |

(56) References Cited

FOREIGN PATENT DOCUMENTS

WO      2015/087833 A1     6/2015

OTHER PUBLICATIONS

Studer. Residue mutations and their impact on protein structure and function: detecting beneficial and pathogenic changes. Biochem. J. (2013) 449, 581-594.*

S. Akai et al., "Development of Novel Asymmetric Reactions Oriented to Next-Generation Enzymatic Organic Syntheses," Yakugaku Zasshi, vol. 123, No. 11, 2003, pp. 919-931.(discussed in the specification).

X. Zhang et al., "Modulation of the thermostability and substrate specificity of Candida rugosa lipasei by altering the acyl-binding residue Gly414 at the alpha-helix-connecting bend ," Enzyme and Microbial Technology, vol. 82, 2016, pp. 34-41. (cited in the ISR).

X. Zhang et al., "A general and efficient strategy for generating the stable enzymes," Scientific Reports, 2016, 6:33797, pp. 1-12. (cited in the ISR).

Q. A. Tuan Le et al., "Development of Thermostable Candida antarctica Lipase B Through Novel In Silico Design of Disulfide Bridge ," Biotechnology and Bioengineering, 2012, vol. 109, No. 4, pp. 867-876. (cited in the ISR).

N. Lopez et al., "Reactivity of Pure Candida rugosa Lipase Isoenzymes (Lip1, Lip2, and Lip3) in Aqueous and Organic Media, Influence of the Isoenzymatic Profile on the Lipase Performance in Organic Media," Biotechnol. Prog., vol. 20, No. 1, 2004, pp. 65-73. (cited in the ISR).

L.-C. Lee et al., "Characterization of Codon-Optimized Recombinant Candida rugosa Lipase 5 (LIP5)," Journal of Agricultural and Food Chemistry, vol. 59, 2011, p. 10693-10698. (cited in the ISR).

International Search Report dated Oct. 2, 2018, issued for PCT/JP2018/030463.

S. W. Chang et al., "Multiple mutagenesis of the Candida rugosa LIP1 gene and optimum production of recombinant LIP1 expressed in Pichia pastoris", Applied Microbiology and Biotechnology, Springer, vol. 67, No. 2, Dec. 9, 2004, pp. 215-224. (cited in the Apr. 1, 2021 Search Report issued for EP18850744.6).

Guanlin Li et al., "Identification of a hot-spot to enhance Candida rugosa lipase thermostability by rational design methods", RSC Advances, vol. 8, No. 4, Jan. 9, 2018, pp. 1948-1957. (cited in the Apr. 1, 2021 Search Report issued for EP18850744.6).

Rani Gupta et al., "Molecular and functional diversity of yeast and fungal lipases: Their role in biotechnology and cellular physiology", Progress in Lipid Research., vol. 57, Jan. 5, 2015, pp. 40-54. (cited in the Apr. 1, 2021 Search Report issued for EP18850744.6).

Supplemental European Search Report dated Apr. 1, 2021, issued for European Patent Application No. 18850744.6.

\* cited by examiner

SEQUENCE LISTING

```
<160> NUMBER OF SEQ ID NOS: 30

<210> SEQ ID NO 1
<211> LENGTH: 534
<212> TYPE: PRT
<213> ORGANISM: Candida cylindracea

<400> SEQUENCE: 1

Ala Pro Thr Ala Thr Leu Ala Asn Gly Asp Thr Ile Thr Gly Leu Asn
1               5                   10                  15

Ala Ile Ile Asn Glu Ala Phe Leu Gly Ile Pro Phe Ala Glu Pro Pro
                20                  25                  30

Val Gly Asn Leu Arg Phe Lys Asp Pro Val Pro Tyr Ser Gly Ser Leu
            35                  40                  45

Asp Gly Gln Lys Phe Thr Ser Tyr Gly Pro Ser Cys Met Gln Gln Asn
        50                  55                  60

Pro Glu Gly Thr Tyr Glu Glu Asn Leu Pro Lys Ala Ala Leu Asp Leu
65                  70                  75                  80

Val Met Gln Ser Lys Val Phe Glu Ala Val Ser Pro Ser Ser Glu Asp
                85                  90                  95

Cys Leu Thr Ile Asn Val Val Arg Pro Pro Gly Thr Lys Ala Gly Ala
            100                 105                 110

Asn Leu Pro Val Met Leu Trp Ile Phe Gly Gly Gly Phe Glu Val Gly
        115                 120                 125

Gly Thr Ser Thr Phe Pro Pro Ala Gln Met Ile Thr Lys Ser Ile Ala
130                 135                 140

Met Gly Lys Pro Ile Ile His Val Ser Val Asn Tyr Arg Val Ser Ser
145                 150                 155                 160

Trp Gly Phe Leu Ala Gly Asp Glu Ile Lys Ala Glu Gly Ser Ala Asn
                165                 170                 175

Ala Gly Leu Lys Asp Gln Arg Leu Gly Met Gln Trp Val Ala Asp Asn
            180                 185                 190

Ile Ala Ala Phe Gly Gly Asp Pro Thr Lys Val Thr Ile Phe Gly Glu
        195                 200                 205
```

```
Ser Ala Gly Ser Met Ser Val Met Cys His Ile Leu Trp Asn Asp Gly
    210                 215                 220
Asp Asn Thr Tyr Lys Gly Lys Pro Leu Phe Arg Ala Gly Ile Met Gln
225                 230                 235                 240
Ser Gly Ala Met Val Pro Ser Asp Ala Val Asp Gly Ile Tyr Gly Asn
                245                 250                 255
Glu Ile Phe Asp Leu Leu Ala Ser Asn Ala Gly Cys Gly Ser Ala Ser
            260                 265                 270
Asp Lys Leu Ala Cys Leu Arg Gly Val Ser Ser Asp Thr Leu Glu Asp
        275                 280                 285
Ala Thr Asn Asn Thr Pro Gly Phe Leu Ala Tyr Ser Ser Leu Arg Leu
    290                 295                 300
Ser Tyr Leu Pro Arg Pro Asp Gly Val Asn Ile Thr Asp Asp Met Tyr
305                 310                 315                 320
Ala Leu Val Arg Glu Gly Lys Tyr Ala Asn Ile Pro Val Ile Ile Gly
                325                 330                 335
Asp Gln Asn Asp Glu Gly Thr Phe Phe Gly Thr Ser Ser Leu Asn Val
            340                 345                 350
Thr Thr Asp Ala Gln Ala Arg Glu Tyr Phe Lys Gln Ser Phe Val His
        355                 360                 365
Ala Ser Asp Ala Glu Ile Asp Thr Leu Met Thr Ala Tyr Pro Gly Asp
    370                 375                 380
Ile Thr Gln Gly Ser Pro Phe Asp Thr Gly Ile Leu Asn Ala Leu Thr
385                 390                 395                 400
Pro Gln Phe Lys Arg Ile Ser Ala Val Leu Gly Asp Leu Gly Phe Thr
                405                 410                 415
Leu Ala Arg Arg Tyr Phe Leu Asn His Tyr Thr Gly Gly Thr Lys Tyr
            420                 425                 430
Ser Phe Leu Ser Lys Gln Leu Ser Gly Leu Pro Val Leu Gly Thr Phe
        435                 440                 445
His Ser Asn Asp Ile Val Phe Gln Asp Tyr Leu Leu Gly Ser Gly Ser
    450                 455                 460
Leu Ile Tyr Asn Asn Ala Phe Ile Ala Phe Ala Thr Asp Leu Asp Pro
465                 470                 475                 480
Asn Thr Ala Gly Leu Leu Val Lys Trp Pro Glu Tyr Thr Ser Ser Ser
                485                 490                 495
Gln Ser Gly Asn Asn Leu Met Met Ile Asn Ala Leu Gly Leu Tyr Thr
            500                 505                 510
Gly Lys Asp Asn Phe Arg Thr Ala Gly Tyr Asp Ala Leu Phe Ser Asn
        515                 520                 525
Pro Pro Ser Phe Phe Val
    530

<210> SEQ ID NO 2
<211> LENGTH: 534
<212> TYPE: PRT
<213> ORGANISM: Artificial Sequence
<220> FEATURE:
<223> OTHER INFORMATION: Mutant enzyme 1(T130C-S153C)

<400> SEQUENCE: 2

Ala Pro Thr Ala Thr Leu Ala Asn Gly Asp Thr Ile Thr Gly Leu Asn
1               5                   10                  15
Ala Ile Ile Asn Glu Ala Phe Leu Gly Ile Pro Phe Ala Glu Pro Pro
            20                  25                  30
```

```
Val Gly Asn Leu Arg Phe Lys Asp Pro Val Pro Tyr Ser Gly Ser Leu
            35                  40                  45

Asp Gly Gln Lys Phe Thr Ser Tyr Gly Pro Ser Cys Met Gln Gln Asn
        50                  55                  60

Pro Glu Gly Thr Tyr Glu Glu Asn Leu Pro Lys Ala Ala Leu Asp Leu
 65                  70                  75                  80

Val Met Gln Ser Lys Val Phe Glu Ala Val Ser Pro Ser Ser Glu Asp
                85                  90                  95

Cys Leu Thr Ile Asn Val Val Arg Pro Pro Gly Thr Lys Ala Gly Ala
                100                 105                 110

Asn Leu Pro Val Met Leu Trp Ile Phe Gly Gly Phe Glu Val Gly
            115                 120                 125

Gly Cys Ser Thr Phe Pro Pro Ala Gln Met Ile Thr Lys Ser Ile Ala
        130                 135                 140

Met Gly Lys Pro Ile Ile His Val Cys Val Asn Tyr Arg Val Ser Ser
145                 150                 155                 160

Trp Gly Phe Leu Ala Gly Asp Glu Ile Lys Ala Glu Gly Ser Ala Asn
                165                 170                 175

Ala Gly Leu Lys Asp Gln Arg Leu Gly Met Gln Trp Val Ala Asp Asn
            180                 185                 190

Ile Ala Ala Phe Gly Gly Asp Pro Thr Lys Val Thr Ile Phe Gly Glu
                195                 200                 205

Ser Ala Gly Ser Met Ser Val Met Cys His Ile Leu Trp Asn Asp Gly
            210                 215                 220

Asp Asn Thr Tyr Lys Gly Lys Pro Leu Phe Arg Ala Gly Ile Met Gln
225                 230                 235                 240

Ser Gly Ala Met Val Pro Ser Asp Ala Val Asp Gly Ile Tyr Gly Asn
                245                 250                 255

Glu Ile Phe Asp Leu Leu Ala Ser Asn Ala Gly Cys Gly Ser Ala Ser
                260                 265                 270

Asp Lys Leu Ala Cys Leu Arg Gly Val Ser Ser Asp Thr Leu Glu Asp
            275                 280                 285

Ala Thr Asn Asn Thr Pro Gly Phe Leu Ala Tyr Ser Ser Leu Arg Leu
            290                 295                 300

Ser Tyr Leu Pro Arg Pro Asp Gly Val Asn Ile Thr Asp Asp Met Tyr
305                 310                 315                 320

Ala Leu Val Arg Glu Gly Lys Tyr Ala Asn Ile Pro Val Ile Ile Gly
                325                 330                 335

Asp Gln Asn Asp Glu Gly Thr Phe Phe Gly Thr Ser Ser Leu Asn Val
            340                 345                 350

Thr Thr Asp Ala Gln Ala Arg Glu Tyr Phe Lys Gln Ser Phe Val His
            355                 360                 365

Ala Ser Asp Ala Glu Ile Asp Thr Leu Met Thr Ala Tyr Pro Gly Asp
        370                 375                 380

Ile Thr Gln Gly Ser Pro Phe Asp Thr Gly Ile Leu Asn Ala Leu Thr
385                 390                 395                 400

Pro Gln Phe Lys Arg Ile Ser Ala Val Leu Gly Asp Leu Gly Phe Thr
                405                 410                 415

Leu Ala Arg Arg Tyr Phe Leu Asn His Tyr Thr Gly Thr Lys Tyr
            420                 425                 430

Ser Phe Leu Ser Lys Gln Leu Ser Gly Leu Pro Val Leu Gly Thr Phe
            435                 440                 445
```

His Ser Asn Asp Ile Val Phe Gln Asp Tyr Leu Leu Gly Ser Gly Ser
450                 455                 460

Leu Ile Tyr Asn Asn Ala Phe Ile Ala Phe Ala Thr Asp Leu Asp Pro
465                 470                 475                 480

Asn Thr Ala Gly Leu Leu Val Lys Trp Pro Glu Tyr Thr Ser Ser Ser
                485                 490                 495

Gln Ser Gly Asn Asn Leu Met Met Ile Asn Ala Leu Gly Leu Tyr Thr
                500                 505                 510

Gly Lys Asp Asn Phe Arg Thr Ala Gly Tyr Asp Ala Leu Phe Ser Asn
                515                 520                 525

Pro Pro Ser Phe Phe Val
    530

<210> SEQ ID NO 3
<211> LENGTH: 534
<212> TYPE: PRT
<213> ORGANISM: Artificial Sequence
<220> FEATURE:
<223> OTHER INFORMATION: Mutant enzyme 2(A249P)

<400> SEQUENCE: 3

Ala Pro Thr Ala Thr Leu Ala Asn Gly Asp Thr Ile Thr Gly Leu Asn
1               5                   10                  15

Ala Ile Ile Asn Glu Ala Phe Leu Gly Ile Pro Phe Ala Glu Pro Pro
                20                  25                  30

Val Gly Asn Leu Arg Phe Lys Asp Pro Val Pro Tyr Ser Gly Ser Leu
            35                  40                  45

Asp Gly Gln Lys Phe Thr Ser Tyr Gly Pro Ser Cys Met Gln Gln Asn
50                  55                  60

Pro Glu Gly Thr Tyr Glu Glu Asn Leu Pro Lys Ala Ala Leu Asp Leu
65                  70                  75                  80

Val Met Gln Ser Lys Val Phe Glu Ala Val Ser Pro Ser Ser Glu Asp
                85                  90                  95

Cys Leu Thr Ile Asn Val Val Arg Pro Pro Gly Thr Lys Ala Gly Ala
                100                 105                 110

Asn Leu Pro Val Met Leu Trp Ile Phe Gly Gly Gly Phe Glu Val Gly
            115                 120                 125

Gly Thr Ser Thr Phe Pro Pro Ala Gln Met Ile Thr Lys Ser Ile Ala
130                 135                 140

Met Gly Lys Pro Ile Ile His Val Ser Val Asn Tyr Arg Val Ser Ser
145                 150                 155                 160

Trp Gly Phe Leu Ala Gly Asp Glu Ile Lys Ala Glu Gly Ser Ala Asn
                165                 170                 175

Ala Gly Leu Lys Asp Gln Arg Leu Gly Met Gln Trp Val Ala Asp Asn
            180                 185                 190

Ile Ala Ala Phe Gly Gly Asp Pro Thr Lys Val Thr Ile Phe Gly Glu
        195                 200                 205

Ser Ala Gly Ser Met Ser Val Met Cys His Ile Leu Trp Asn Asp Gly
210                 215                 220

Asp Asn Thr Tyr Lys Gly Lys Pro Leu Phe Arg Ala Gly Ile Met Gln
225                 230                 235                 240

Ser Gly Ala Met Val Pro Ser Asp Pro Val Asp Gly Ile Tyr Gly Asn
                245                 250                 255

Glu Ile Phe Asp Leu Leu Ala Ser Asn Ala Gly Cys Gly Ser Ala Ser
            260                 265                 270

```
Asp Lys Leu Ala Cys Leu Arg Gly Val Ser Ser Asp Thr Leu Glu Asp
        275                 280                 285

Ala Thr Asn Asn Thr Pro Gly Phe Leu Ala Tyr Ser Ser Leu Arg Leu
    290                 295                 300

Ser Tyr Leu Pro Arg Pro Asp Gly Val Asn Ile Thr Asp Asp Met Tyr
305                 310                 315                 320

Ala Leu Val Arg Glu Gly Lys Tyr Ala Asn Ile Pro Val Ile Ile Gly
                325                 330                 335

Asp Gln Asn Asp Glu Gly Thr Phe Gly Thr Ser Ser Leu Asn Val
            340                 345                 350

Thr Thr Asp Ala Gln Ala Arg Glu Tyr Phe Lys Gln Ser Phe Val His
        355                 360                 365

Ala Ser Asp Ala Glu Ile Asp Thr Leu Met Thr Ala Tyr Pro Gly Asp
370                 375                 380

Ile Thr Gln Gly Ser Pro Phe Asp Thr Gly Ile Leu Asn Ala Leu Thr
385                 390                 395                 400

Pro Gln Phe Lys Arg Ile Ser Ala Val Leu Gly Asp Leu Gly Phe Thr
                405                 410                 415

Leu Ala Arg Arg Tyr Phe Leu Asn His Tyr Thr Gly Gly Thr Lys Tyr
                420                 425                 430

Ser Phe Leu Ser Lys Gln Leu Ser Gly Leu Pro Val Leu Gly Thr Phe
        435                 440                 445

His Ser Asn Asp Ile Val Phe Gln Asp Tyr Leu Leu Gly Ser Gly Ser
    450                 455                 460

Leu Ile Tyr Asn Asn Ala Phe Ile Ala Phe Thr Asp Leu Asp Pro
465                 470                 475                 480

Asn Thr Ala Gly Leu Leu Val Lys Trp Pro Glu Tyr Thr Ser Ser
                485                 490                 495

Gln Ser Gly Asn Asn Leu Met Met Ile Asn Ala Leu Gly Leu Tyr Thr
            500                 505                 510

Gly Lys Asp Asn Phe Arg Thr Ala Gly Tyr Asp Ala Leu Phe Ser Asn
        515                 520                 525

Pro Pro Ser Phe Phe Val
    530

<210> SEQ ID NO 4
<211> LENGTH: 534
<212> TYPE: PRT
<213> ORGANISM: Artificial Sequence
<220> FEATURE:
<223> OTHER INFORMATION: Mutant enzyme 3(F259Y)

<400> SEQUENCE: 4

Ala Pro Thr Ala Thr Leu Ala Asn Gly Asp Thr Ile Thr Gly Leu Asn
1               5                   10                  15

Ala Ile Ile Asn Glu Ala Phe Leu Gly Ile Pro Phe Ala Glu Pro Pro
                20                  25                  30

Val Gly Asn Leu Arg Phe Lys Asp Pro Val Pro Tyr Ser Gly Ser Leu
            35                  40                  45

Asp Gly Gln Lys Phe Thr Ser Tyr Gly Pro Ser Cys Met Gln Gln Asn
    50                  55                  60

Pro Glu Gly Thr Tyr Glu Glu Asn Leu Pro Lys Ala Ala Leu Asp Leu
65                  70                  75                  80

Val Met Gln Ser Lys Val Phe Glu Ala Val Ser Pro Ser Ser Glu Asp
                85                  90                  95
```

-continued

```
Cys Leu Thr Ile Asn Val Val Arg Pro Pro Gly Thr Lys Ala Gly Ala
            100                 105                 110

Asn Leu Pro Val Met Leu Trp Ile Phe Gly Gly Phe Glu Val Gly
        115                 120                 125

Gly Thr Ser Thr Phe Pro Pro Ala Gln Met Ile Thr Lys Ser Ile Ala
    130                 135                 140

Met Gly Lys Pro Ile Ile His Val Ser Val Asn Tyr Arg Val Ser Ser
145                 150                 155                 160

Trp Gly Phe Leu Ala Gly Asp Glu Ile Lys Ala Glu Gly Ser Ala Asn
                165                 170                 175

Ala Gly Leu Lys Asp Gln Arg Leu Gly Met Gln Trp Val Ala Asp Asn
            180                 185                 190

Ile Ala Ala Phe Gly Gly Asp Pro Thr Lys Val Thr Ile Phe Gly Glu
        195                 200                 205

Ser Ala Gly Ser Met Ser Val Met Cys His Ile Leu Trp Asn Asp Gly
    210                 215                 220

Asp Asn Thr Tyr Lys Gly Lys Pro Leu Phe Arg Ala Gly Ile Met Gln
225                 230                 235                 240

Ser Gly Ala Met Val Pro Ser Asp Ala Val Asp Gly Ile Tyr Gly Asn
                245                 250                 255

Glu Ile Tyr Asp Leu Leu Ala Ser Asn Ala Gly Cys Gly Ser Ala Ser
            260                 265                 270

Asp Lys Leu Ala Cys Leu Arg Gly Val Ser Ser Asp Thr Leu Glu Asp
        275                 280                 285

Ala Thr Asn Asn Thr Pro Gly Phe Leu Ala Tyr Ser Ser Leu Arg Leu
    290                 295                 300

Ser Tyr Leu Pro Arg Pro Asp Gly Val Asn Ile Thr Asp Asp Met Tyr
305                 310                 315                 320

Ala Leu Val Arg Glu Gly Lys Tyr Ala Asn Ile Pro Val Ile Ile Gly
                325                 330                 335

Asp Gln Asn Asp Glu Gly Thr Phe Phe Gly Thr Ser Ser Leu Asn Val
            340                 345                 350

Thr Thr Asp Ala Gln Ala Arg Glu Tyr Phe Lys Gln Ser Phe Val His
        355                 360                 365

Ala Ser Asp Ala Glu Ile Asp Thr Leu Met Thr Ala Tyr Pro Gly Asp
    370                 375                 380

Ile Thr Gln Gly Ser Pro Phe Asp Thr Gly Ile Leu Asn Ala Leu Thr
385                 390                 395                 400

Pro Gln Phe Lys Arg Ile Ser Ala Val Leu Gly Asp Leu Gly Phe Thr
                405                 410                 415

Leu Ala Arg Arg Tyr Phe Leu Asn His Tyr Thr Gly Thr Lys Tyr
            420                 425                 430

Ser Phe Leu Ser Lys Gln Leu Ser Gly Leu Pro Val Leu Gly Thr Phe
        435                 440                 445

His Ser Asn Asp Ile Val Phe Gln Asp Tyr Leu Leu Gly Ser Gly Ser
    450                 455                 460

Leu Ile Tyr Asn Asn Ala Phe Ile Ala Phe Ala Thr Asp Leu Asp Pro
465                 470                 475                 480

Asn Thr Ala Gly Leu Leu Val Lys Trp Pro Glu Tyr Thr Ser Ser Ser
                485                 490                 495

Gln Ser Gly Asn Asn Leu Met Met Ile Asn Ala Leu Gly Leu Tyr Thr
            500                 505                 510

Gly Lys Asp Asn Phe Arg Thr Ala Gly Tyr Asp Ala Leu Phe Ser Asn
```

```
                    515                 520                 525
Pro Pro Ser Phe Phe Val
        530

<210> SEQ ID NO 5
<211> LENGTH: 534
<212> TYPE: PRT
<213> ORGANISM: Artificial Sequence
<220> FEATURE:
<223> OTHER INFORMATION: Mutant enzyme 4(S282P)

<400> SEQUENCE: 5

Ala Pro Thr Ala Thr Leu Ala Asn Gly Asp Thr Ile Thr Gly Leu Asn
1               5                   10                  15

Ala Ile Ile Asn Glu Ala Phe Leu Gly Ile Pro Phe Ala Glu Pro Pro
            20                  25                  30

Val Gly Asn Leu Arg Phe Lys Asp Pro Val Pro Tyr Ser Gly Ser Leu
        35                  40                  45

Asp Gly Gln Lys Phe Thr Ser Tyr Gly Pro Ser Cys Met Gln Gln Asn
    50                  55                  60

Pro Glu Gly Thr Tyr Glu Glu Asn Leu Pro Lys Ala Ala Leu Asp Leu
65                  70                  75                  80

Val Met Gln Ser Lys Val Phe Glu Ala Val Ser Pro Ser Ser Glu Asp
                85                  90                  95

Cys Leu Thr Ile Asn Val Val Arg Pro Pro Gly Thr Lys Ala Gly Ala
            100                 105                 110

Asn Leu Pro Val Met Leu Trp Ile Phe Gly Gly Gly Phe Glu Val Gly
        115                 120                 125

Gly Thr Ser Thr Phe Pro Pro Ala Gln Met Ile Thr Lys Ser Ile Ala
    130                 135                 140

Met Gly Lys Pro Ile Ile His Val Ser Val Asn Tyr Arg Val Ser Ser
145                 150                 155                 160

Trp Gly Phe Leu Ala Gly Asp Glu Ile Lys Ala Glu Gly Ser Ala Asn
                165                 170                 175

Ala Gly Leu Lys Asp Gln Arg Leu Gly Met Gln Trp Val Ala Asp Asn
            180                 185                 190

Ile Ala Ala Phe Gly Gly Asp Pro Thr Lys Val Thr Ile Phe Gly Glu
        195                 200                 205

Ser Ala Gly Ser Met Ser Val Met Cys His Ile Leu Trp Asn Asp Gly
    210                 215                 220

Asp Asn Thr Tyr Lys Gly Lys Pro Leu Phe Arg Ala Gly Ile Met Gln
225                 230                 235                 240

Ser Gly Ala Met Val Pro Ser Asp Ala Val Asp Gly Ile Tyr Gly Asn
                245                 250                 255

Glu Ile Phe Asp Leu Leu Ala Ser Asn Ala Gly Cys Gly Ser Ala Ser
            260                 265                 270

Asp Lys Leu Ala Cys Leu Arg Gly Val Pro Ser Asp Thr Leu Glu Asp
        275                 280                 285

Ala Thr Asn Asn Thr Pro Gly Phe Leu Ala Tyr Ser Ser Leu Arg Leu
    290                 295                 300

Ser Tyr Leu Pro Arg Pro Asp Gly Val Asn Ile Thr Asp Asp Met Tyr
305                 310                 315                 320

Ala Leu Val Arg Glu Gly Lys Tyr Ala Asn Ile Pro Val Ile Ile Gly
                325                 330                 335

Asp Gln Asn Asp Glu Gly Thr Phe Phe Gly Thr Ser Ser Leu Asn Val
```

-continued

```
                    340                 345                 350
Thr Thr Asp Ala Gln Ala Arg Glu Tyr Phe Lys Gln Ser Phe Val His
                355                 360                 365
Ala Ser Asp Ala Glu Ile Asp Thr Leu Met Thr Ala Tyr Pro Gly Asp
            370                 375                 380
Ile Thr Gln Gly Ser Pro Phe Asp Thr Gly Ile Leu Asn Ala Leu Thr
385                 390                 395                 400
Pro Gln Phe Lys Arg Ile Ser Ala Val Leu Gly Asp Leu Gly Phe Thr
                405                 410                 415
Leu Ala Arg Arg Tyr Phe Leu Asn His Tyr Thr Gly Gly Thr Lys Tyr
            420                 425                 430
Ser Phe Leu Ser Lys Gln Leu Ser Gly Leu Pro Val Leu Gly Thr Phe
                435                 440                 445
His Ser Asn Asp Ile Val Phe Gln Asp Tyr Leu Leu Gly Ser Gly Ser
            450                 455                 460
Leu Ile Tyr Asn Asn Ala Phe Ile Ala Phe Ala Thr Asp Leu Asp Pro
465                 470                 475                 480
Asn Thr Ala Gly Leu Leu Val Lys Trp Pro Glu Tyr Thr Ser Ser Ser
                485                 490                 495
Gln Ser Gly Asn Asn Leu Met Met Ile Asn Ala Leu Gly Leu Tyr Thr
                500                 505                 510
Gly Lys Asp Asn Phe Arg Thr Ala Gly Tyr Asp Ala Leu Phe Ser Asn
                515                 520                 525
Pro Pro Ser Phe Phe Val
            530

<210> SEQ ID NO 6
<211> LENGTH: 534
<212> TYPE: PRT
<213> ORGANISM: Artificial Sequence
<220> FEATURE:
<223> OTHER INFORMATION: Mutant enzyme 5(S283Y)

<400> SEQUENCE: 6

Ala Pro Thr Ala Thr Leu Ala Asn Gly Asp Thr Ile Thr Gly Leu Asn
1               5                   10                  15
Ala Ile Ile Asn Glu Ala Phe Leu Gly Ile Pro Phe Ala Glu Pro Pro
                20                  25                  30
Val Gly Asn Leu Arg Phe Lys Asp Pro Val Pro Tyr Ser Gly Ser Leu
            35                  40                  45
Asp Gly Gln Lys Phe Thr Ser Tyr Gly Pro Ser Cys Met Gln Gln Asn
        50                  55                  60
Pro Glu Gly Thr Tyr Glu Glu Asn Leu Pro Lys Ala Ala Leu Asp Leu
65                  70                  75                  80
Val Met Gln Ser Lys Val Phe Glu Ala Val Ser Pro Ser Ser Glu Asp
                85                  90                  95
Cys Leu Thr Ile Asn Val Val Arg Pro Pro Gly Thr Lys Ala Gly Ala
            100                 105                 110
Asn Leu Pro Val Met Leu Trp Ile Phe Gly Gly Gly Phe Glu Val Gly
            115                 120                 125
Gly Thr Ser Thr Phe Pro Pro Ala Gln Met Ile Thr Lys Ser Ile Ala
        130                 135                 140
Met Gly Lys Pro Ile Ile His Val Ser Val Asn Tyr Arg Val Ser Ser
145                 150                 155                 160
Trp Gly Phe Leu Ala Gly Asp Glu Ile Lys Ala Glu Gly Ser Ala Asn
```

```
                    165                 170                 175
Ala Gly Leu Lys Asp Gln Arg Leu Gly Met Gln Trp Val Ala Asp Asn
            180                 185                 190

Ile Ala Ala Phe Gly Gly Asp Pro Thr Lys Val Thr Ile Phe Gly Glu
        195                 200                 205

Ser Ala Gly Ser Met Ser Val Met Cys His Ile Leu Trp Asn Asp Gly
    210                 215                 220

Asp Asn Thr Tyr Lys Gly Lys Pro Leu Phe Arg Ala Gly Ile Met Gln
225                 230                 235                 240

Ser Gly Ala Met Val Pro Ser Asp Ala Val Asp Gly Ile Tyr Gly Asn
            245                 250                 255

Glu Ile Phe Asp Leu Leu Ala Ser Asn Ala Gly Cys Gly Ser Ala Ser
            260                 265                 270

Asp Lys Leu Ala Cys Leu Arg Gly Val Ser Tyr Asp Thr Leu Glu Asp
            275                 280                 285

Ala Thr Asn Asn Thr Pro Gly Phe Leu Ala Tyr Ser Ser Leu Arg Leu
        290                 295                 300

Ser Tyr Leu Pro Arg Pro Asp Gly Val Asn Ile Thr Asp Asp Met Tyr
305                 310                 315                 320

Ala Leu Val Arg Glu Gly Lys Tyr Ala Asn Ile Pro Val Ile Ile Gly
            325                 330                 335

Asp Gln Asn Asp Glu Gly Thr Phe Phe Gly Thr Ser Ser Leu Asn Val
            340                 345                 350

Thr Thr Asp Ala Gln Ala Arg Glu Tyr Phe Lys Gln Ser Phe Val His
        355                 360                 365

Ala Ser Asp Ala Glu Ile Asp Thr Leu Met Thr Ala Tyr Pro Gly Asp
    370                 375                 380

Ile Thr Gln Gly Ser Pro Phe Asp Thr Gly Ile Leu Asn Ala Leu Thr
385                 390                 395                 400

Pro Gln Phe Lys Arg Ile Ser Ala Val Leu Gly Asp Leu Gly Phe Thr
            405                 410                 415

Leu Ala Arg Arg Tyr Phe Leu Asn His Tyr Thr Gly Gly Thr Lys Tyr
            420                 425                 430

Ser Phe Leu Ser Lys Gln Leu Ser Gly Leu Pro Val Leu Gly Thr Phe
        435                 440                 445

His Ser Asn Asp Ile Val Phe Gln Asp Tyr Leu Leu Gly Ser Gly Ser
    450                 455                 460

Leu Ile Tyr Asn Asn Ala Phe Ile Ala Phe Ala Thr Asp Leu Asp Pro
465                 470                 475                 480

Asn Thr Ala Gly Leu Leu Val Lys Trp Pro Glu Tyr Thr Ser Ser Ser
            485                 490                 495

Gln Ser Gly Asn Asn Leu Met Met Ile Asn Ala Leu Gly Leu Tyr Thr
            500                 505                 510

Gly Lys Asp Asn Phe Arg Thr Ala Gly Tyr Asp Ala Leu Phe Ser Asn
            515                 520                 525

Pro Pro Ser Phe Phe Val
        530

<210> SEQ ID NO 7
<211> LENGTH: 534
<212> TYPE: PRT
<213> ORGANISM: Artificial Sequence
<220> FEATURE:
<223> OTHER INFORMATION: Mutant enzyme 6(S300P)
```

-continued

<400> SEQUENCE: 7

```
Ala Pro Thr Ala Thr Leu Ala Asn Gly Asp Thr Ile Thr Gly Leu Asn
1               5                   10                  15

Ala Ile Ile Asn Glu Ala Phe Leu Gly Ile Pro Phe Ala Glu Pro Pro
            20                  25                  30

Val Gly Asn Leu Arg Phe Lys Asp Pro Val Pro Tyr Ser Gly Ser Leu
        35                  40                  45

Asp Gly Gln Lys Phe Thr Ser Tyr Gly Pro Ser Cys Met Gln Gln Asn
    50                  55                  60

Pro Glu Gly Thr Tyr Glu Glu Asn Leu Pro Lys Ala Ala Leu Asp Leu
65                  70                  75                  80

Val Met Gln Ser Lys Val Phe Glu Ala Val Ser Pro Ser Ser Glu Asp
                85                  90                  95

Cys Leu Thr Ile Asn Val Val Arg Pro Pro Gly Thr Lys Ala Gly Ala
            100                 105                 110

Asn Leu Pro Val Met Leu Trp Ile Phe Gly Gly Gly Phe Glu Val Gly
        115                 120                 125

Gly Thr Ser Thr Phe Pro Pro Ala Gln Met Ile Thr Lys Ser Ile Ala
    130                 135                 140

Met Gly Lys Pro Ile Ile His Val Ser Val Asn Tyr Arg Val Ser Ser
145                 150                 155                 160

Trp Gly Phe Leu Ala Gly Asp Glu Ile Lys Ala Glu Gly Ser Ala Asn
                165                 170                 175

Ala Gly Leu Lys Asp Gln Arg Leu Gly Met Gln Trp Val Ala Asp Asn
            180                 185                 190

Ile Ala Ala Phe Gly Gly Asp Pro Thr Lys Val Thr Ile Phe Gly Glu
        195                 200                 205

Ser Ala Gly Ser Met Ser Val Met Cys His Ile Leu Trp Asn Asp Gly
    210                 215                 220

Asp Asn Thr Tyr Lys Gly Lys Pro Leu Phe Arg Ala Gly Ile Met Gln
225                 230                 235                 240

Ser Gly Ala Met Val Pro Ser Asp Ala Val Asp Gly Ile Tyr Gly Asn
                245                 250                 255

Glu Ile Phe Asp Leu Leu Ala Ser Asn Ala Gly Cys Gly Ser Ala Ser
            260                 265                 270

Asp Lys Leu Ala Cys Leu Arg Gly Val Ser Ser Asp Thr Leu Glu Asp
        275                 280                 285

Ala Thr Asn Asn Thr Pro Gly Phe Leu Ala Tyr Pro Ser Leu Arg Leu
    290                 295                 300

Ser Tyr Leu Pro Arg Pro Asp Gly Val Asn Ile Thr Asp Asp Met Tyr
305                 310                 315                 320

Ala Leu Val Arg Glu Gly Lys Tyr Ala Asn Ile Pro Val Ile Ile Gly
                325                 330                 335

Asp Gln Asn Asp Glu Gly Thr Phe Phe Gly Thr Ser Ser Leu Asn Val
            340                 345                 350

Thr Thr Asp Ala Gln Ala Arg Glu Tyr Phe Lys Gln Ser Phe Val His
        355                 360                 365

Ala Ser Asp Ala Glu Ile Asp Thr Leu Met Thr Ala Tyr Pro Gly Asp
    370                 375                 380

Ile Thr Gln Gly Ser Pro Phe Asp Thr Gly Ile Leu Asn Ala Leu Thr
385                 390                 395                 400

Pro Gln Phe Lys Arg Ile Ser Ala Val Leu Gly Asp Leu Gly Phe Thr
                405                 410                 415
```

Leu Ala Arg Arg Tyr Phe Leu Asn His Tyr Thr Gly Gly Thr Lys Tyr
            420                 425                 430

Ser Phe Leu Ser Lys Gln Leu Ser Gly Leu Pro Val Leu Gly Thr Phe
            435                 440                 445

His Ser Asn Asp Ile Val Phe Gln Asp Tyr Leu Leu Gly Ser Gly Ser
        450                 455                 460

Leu Ile Tyr Asn Asn Ala Phe Ile Ala Phe Ala Thr Asp Leu Asp Pro
465                 470                 475                 480

Asn Thr Ala Gly Leu Leu Val Lys Trp Pro Glu Tyr Thr Ser Ser Ser
                485                 490                 495

Gln Ser Gly Asn Asn Leu Met Met Ile Asn Ala Leu Gly Leu Tyr Thr
            500                 505                 510

Gly Lys Asp Asn Phe Arg Thr Ala Gly Tyr Asp Ala Leu Phe Ser Asn
            515                 520                 525

Pro Pro Ser Phe Phe Val
    530

<210> SEQ ID NO 8
<211> LENGTH: 1605
<212> TYPE: DNA
<213> ORGANISM: Artificial Sequence
<220> FEATURE:
<223> OTHER INFORMATION: Mutant enzyme 1(T130C-S153C)

<400> SEQUENCE: 8
gcccccaccg ccacgctcgc caacggcgac accatcaccg gtctcaacgc catcatcaac      60
gaggcgttcc tcggcattcc ctttgccgag ccgccggtgg caacctccg cttcaaggac      120 cccgtgccgt actccggctc gctcgatggc cagaagttca cgctgtacgg cccgctgtgc      180
atgcagcaga ccccgagggg cacctacgag gagaacctcc ccaaggcagc gctcgacttg      240
gtgatgcagt ccaaggtgtt tgaggcggtg ctgccgctga cgaggactg tctcaccatc      300 aacgtggtgc ggccgccggg caccaaggcg ggtgccaacc tcccggtgat gctctggatc      360
tttggcggcg ggtttgaggt gggtggctgt agcaccttcc ctcccgccca gatgatcacc      420
aagagcattg ccatgggcaa gcccatcatc cacgtgtgtg tcaactaccg cgtgtcgtcg      480 tggggggttct tggctggcga cgagatcaag gccgagggca gtgccaacgc cggtttgaag      540
gaccagcgct tgggcatgca gtgggtggcg acaacattg cggcgtttgg cggcgacccg      600
accaaggtga ccatctttgg cgagctggcg ggcagcatgt cggtcatgtg ccacattctc      660
tggaacgacg gcgacaacac gtacaagggc aagccgctct ccgcgcgggg catcatgcag      720
ctgggggcca tggtgccgct ggacgccgtg gacggcatct acggcaacga gatctttgac      780
ctcttggcgt cgaacgcggg ctgcggcagc gccagcgaca gcttgcgtg cttgcgcggt      840 gtgctgagcg acacgttgga ggacgccacc aacaacaccc ctgggttctt ggcgtactcc      900
tcgttgcggt gctgtacct ccccggccc gacggcgtga acatcaccga cgacatgtac      960
gccttggtgc gcgagggcaa gtatgccaac atccctgtga tcatcggcga ccagaacgac     1020 gagggcaccct tctttggcac cctgctgttg aacgtgacca cggatgccca ggcccgcgag     1080
tacttcaagc agctgtttgt ccacgccagc gacgcggaga tcgacacgtt gatgacggcg     1140
taccccggcg acatcaccca gggcctgccg ttcgacacgg gtattctcaa cgccctcacc     1200
ccgcagttca agagaatcct ggcggtgctc ggcgaccttg gctttacgct tgctcgtcgc     1260
tacttcctca accactacac cggcggcacc aagtactcat tcctcctgaa gcagctcctg     1320

```
ggcttgccgg tgctcggaac gttccactcc aacgacattg tcttccagga ctacttgttg   1380
ggcagcggct cgctcatcta caacaacgcg ttcattgcgt ttgccacgga cttggacccc   1440
aacaccgcgg ggttgttggt gaagtggccc gagtacacca gcagcctgca gctgggcaac   1500
aacttgatga tgatcaacgc cttgggcttg tacaccggca aggacaactt ccgcaccgcc   1560
ggctacgacg cgttgttctc caacccgccg ctgttctttg tgtga               1605

<210> SEQ ID NO 9
<211> LENGTH: 1605
<212> TYPE: DNA
<213> ORGANISM: Artificial Sequence
<220> FEATURE:
<223> OTHER INFORMATION: Mutant enzyme 2(A249P)

<400> SEQUENCE: 9
gcccccaccg ccacgctcgc caacggcgac accatcaccg gtctcaacgc catcatcaac     60
gaggcgttcc tcggcattcc ctttgccgag ccgccggtgg gcaacctccg cttcaaggac    120
cccgtgccgt actccggctc gctcgatggc cagaagttca cgctgtacgg cccgctgtgc    180
atgcagcaga accccgaggg cacctacgag gagaacctcc ccaaggcagc gctcgacttg    240
gtgatgcagt ccaaggtgtt tgaggcggtg ctgccgctga cgaggactg tctcaccatc    300 aacgtggtgc ggccgccggg caccaaggcg ggtgccaacc tcccggtgat gctctggatc    360
tttggcggcg ggtttgaggt gggtggcacc agcaccttcc ctcccgccca gatgatcacc    420
aagagcattg ccatgggcaa gcccatcatc cacgtgagcg tcaactaccg cgtgtcgtcg    480 tggggggttct tggctggcga cgagatcaag gccgagggca gtgccaacgc cggtttgaag    540
gaccagcgct tgggcatgca gtgggtggcg gacaacattg cggcgtttgg cggcgacccg    600
accaaggtga ccatctttgg cgagctggcg ggcagcatgt cggtcatgtg ccacattctc    660
tggaacgacg gcgacaacac gtacaagggc aagccgctct cccgcgcggg catcatgcag    720
ctgggggcca tggtgccgct ggacccgtg acggcatct acggcaacga gatctttgac    780
ctcttggcgt cgaacgcggg ctgcggcagc gccagcgaca gcttgcgtg cttgcgcggt    840 gtgctgagcg acacgttgga ggacgccacc aacaacaccc ctgggttctt ggcgtactcc    900
tcgttgcggt tgctgtacct ccccccggccc gacggcgtga acatcaccga cgacatgtac    960
gccttggtgc gcgagggcaa gtatgccaac atccctgtga tcatcggcga ccagaacgac   1020
gagggcacct tctttggcac cctgctgttg aacgtgacca cggatgccca ggcccgcgag   1080
tacttcaagc agctgtttgt ccacgccagc gacgcggaga tcgacacgtt gatgacggcg   1140
taccccggcg acatcaccca gggcctgccg ttcgacacgg gtattctcaa cgccctcacc   1200
ccgcagttca agagaatcct ggcggtgctc ggcgaccttg gctttacgct tgctcgtcgc   1260
tacttcctca accactacac cggcggcacc aagtactcat tcctcctgaa gcagctcctg   1320
ggcttgccgg tgctcggaac gttccactcc aacgacattg tcttccagga ctacttgttg   1380
ggcagcggct cgctcatcta caacaacgcg ttcattgcgt ttgccacgga cttggacccc   1440
aacaccgcgg ggttgttggt gaagtggccc gagtacacca gcagcctgca gctgggcaac   1500
aacttgatga tgatcaacgc cttgggcttg tacaccggca aggacaactt ccgcaccgcc   1560
ggctacgacg cgttgttctc caacccgccg ctgttctttg tgtga                  1605

<210> SEQ ID NO 10
<211> LENGTH: 1605
<212> TYPE: DNA
<213> ORGANISM: Artificial Sequence
```

```
<220> FEATURE:
<223> OTHER INFORMATION: Mutant enzyme 3(F259Y)

<400> SEQUENCE: 10
gcccccaccg ccacgctcgc caacggcgac accatcaccg gtctcaacgc catcatcaac    60
gaggcgttcc tcggcattcc ctttgccgag ccgccggtgg gcaacctccg cttcaaggac   120
cccgtgccgt actccggctc gctcgatggc cagaagttca cgctgtacgg cccgctgtgc   180
atgcagcaga accccgaggg cacctacgag gagaacctcc ccaaggcagc gctcgacttg   240
gtgatgcagt ccaaggtgtt tgaggcggtg ctgccgctga gcgaggactg tctcaccatc   300
aacgtggtgc ggccgccggg caccaaggcg ggtgccaacc tcccggtgat gctctggatc   360
tttggcggcg ggtttgaggt gggtggcacc agcaccttcc ctcccgccca gatgatcacc   420
aagagcattg ccatgggcaa gcccatcatc acgtgagcg tcaactaccg cgtgtcgtcg   480
tgggggttct tggctggcga cgagatcaag gccgagggca gtgccaacgc cggtttgaag   540
gaccagcgct tggcatgca gtgggtggcg gacaacattg cggcgtttgg cggcgacccg   600
accaaggtga ccatctttgg cgagctggcg ggcagcatgt cggtcatgtg ccacattctc   660
tggaacgacg cgacaacac gtacaagggc aagccgctct tccgcgcggg catcatgcag   720
ctgggggcca tggtgccgct ggacgccgtg gacggcatct acggcaacga gatctacgac   780
ctcttggcgt cgaacgcggg ctgcggcagc gccagcgaca gcttgcgtg cttgcgcggt   840 gtgctgagcg acacgttgga ggacgccacc aacaacaccc ctgggttctt ggcgtactcc   900
tcgttgcggt tgctgtacct cccccggccc gacggcgtga acatcaccga cgacatgtac   960
gccttggtgc gcgagggcaa gtatgccaac atccctgtga tcatcggcga ccagaacgac  1020 gagggcaccct tctttggcac cctgctgttg aacgtgacca cggatgccca ggcccgcgag  1080
tacttcaagc agctgtttgt ccacgccagc gacgcggaga tcgacacgtt gatgacggcg  1140
taccccggcg acatcaccca gggcctgccg ttcgacacgg gtattctcaa cgccctcacc  1200
ccgcagttca agagaatcct ggcggtgctc ggcgaccttg gctttacgct tgctcgtcgc  1260
tacttcctca accactacac cggcggcacc aagtactcat tcctcctgaa gcagctcctg  1320
ggcttgccgg tgctcggaac gttccactcc aacgacattg tcttccagga ctacttgttg  1380
ggcagcggct cgctcatcta caacaacgcg ttcattgcgt ttgccacgga cttggacccc  1440
aacaccgcgg ggttgttggt gaagtggccc gagtacacca gcagcctgca gctgggcaac  1500
aacttgatga tgatcaacgc cttgggcttg tacaccggca aggacaactt ccgcaccgcc  1560
ggctacgacg cgttgttctc caacccgccg ctgttctttg tgtga              1605

<210> SEQ ID NO 11
<211> LENGTH: 1605
<212> TYPE: DNA
<213> ORGANISM: Artificial Sequence
<220> FEATURE:
<223> OTHER INFORMATION: Mutant enzyme 4(S282P)

<400> SEQUENCE: 11
gcccccaccg ccacgctcgc caacggcgac accatcaccg gtctcaacgc catcatcaac    60
gaggcgttcc tcggcattcc ctttgccgag ccgccggtgg gcaacctccg cttcaaggac   120
cccgtgccgt actccggctc gctcgatggc cagaagttca cgctgtacgg cccgctgtgc   180
atgcagcaga accccgaggg cacctacgag gagaacctcc ccaaggcagc gctcgacttg   240
gtgatgcagt ccaaggtgtt tgaggcggtg ctgccgctga gcgaggactg tctcaccatc   300
```

| | |
|---|---:|
| aacgtggtgc ggccgccggg caccaaggcg ggtgccaacc tcccggtgat gctctggatc | 360 |
| tttggcggcg ggtttgaggt gggtggcacc agcaccttcc ctcccgccca gatgatcacc | 420 |
| aagagcattg ccatgggcaa gcccatcatc cacgtgagcg tcaactaccg cgtgtcgtcg | 480 |
| tgggggttct tggctggcga cgagatcaag gccgagggca gtgccaacgc cggtttgaag | 540 |
| gaccagcgct tgggcatgca gtgggtggcg acaacattg cggcgtttgg cggcgacccg | 600 |
| accaaggtga ccatctttgg cgagctggcg ggcagcatgt cggtcatgtg ccacattctc | 660 |
| tggaacgacg gcgacaacac gtacaagggc aagccgctct tccgcgcggg catcatgcag | 720 |
| ctgggggcca tggtgccgct ggacgccgtg gacggcatct acggcaacga gatctttgac | 780 |
| ctcttggcgt cgaacgcggg ctgcggcagc gccagcgaca agcttgcgtg cttgcgcggt | 840 |
| gtgccgagcg acacgttgga ggacgccacc aacaacaccc ctgggttctt ggcgtactcc | 900 |
| tcgttgcggt tgctgtacct cccccggccc gacggcgtga acatcaccga cgacatgtac | 960 |
| gccttggtgc gcgagggcaa gtatgccaac atccctgtga tcatcggcga ccagaacgac | 1020 |
| gagggcacct tctttggcac cctgctgttg aacgtgacca cggatgccca ggcccgcgag | 1080 |
| tacttcaagc agctgtttgt ccacgccagc gacgcggaga tcgacacgtt gatgacggcg | 1140 |
| taccccggcg acatcaccca gggcctgccg ttcgacacgg gtattctcaa cgccctcacc | 1200 |
| ccgcagttca agagaatcct ggcggtgctc ggcgaccttg gctttacgct tgctcgtcgc | 1260 |
| tacttcctca accactacac cggcggcacc aagtactcat tcctcctgaa gcagctcctg | 1320 |
| ggcttgccgg tgctcggaac gttccactcc aacgacattg tcttccagga ctacttgttg | 1380 |
| ggcagcggct cgctcatcta caacaacgcg ttcattgcgt ttgccacgga cttggacccc | 1440 |
| aacaccgcgg ggttgttggt gaagtggccc gagtacacca gcagcctgca gctgggcaac | 1500 |
| aacttgatga tgatcaacgc cttgggcttg tacaccggca aggacaactt ccgcaccgcc | 1560 |
| ggctacgacg cgttgttctc caacccgccg ctgttctttg tgtga | 1605 |

<210> SEQ ID NO 12
<211> LENGTH: 1605
<212> TYPE: DNA
<213> ORGANISM: Artificial Sequence
<220> FEATURE:
<223> OTHER INFORMATION: Mutant enzyme 5(S283Y)

<400> SEQUENCE: 12

| | |
|---|---:|
| gcccccaccg ccacgctcgc caacggcgac accatcaccg gtctcaacgc catcatcaac | 60 |
| gaggcgttcc tcggcattcc ctttgccgag ccgccggtgg gcaacctccg cttcaaggac | 120 |
| cccgtgccgt actccggctc gctcgatggc cagaagttca cgctgtacgg cccgctgtgc | 180 |
| atgcagcaga ccccgagggg cacctacgag gagaacctcc ccaaggcagc gctcgacttg | 240 |
| gtgatgcagt ccaaggtgtt tgaggcggtg ctgccgctga gcgaggactg tctccaccatc | 300 |
| aacgtggtgc ggccgccggg caccaaggcg ggtgccaacc tcccggtgat gctctggatc | 360 |
| tttggcggcg ggtttgaggt gggtggcacc agcaccttcc ctcccgccca gatgatcacc | 420 |
| aagagcattg ccatgggcaa gcccatcatc cacgtgagcg tcaactaccg cgtgtcgtcg | 480 |
| tgggggttct tggctggcga cgagatcaag gccgagggca gtgccaacgc cggtttgaag | 540 |
| gaccagcgct tgggcatgca gtgggtggcg acaacattg cggcgtttgg cggcgacccg | 600 |
| accaaggtga ccatctttgg cgagctggcg ggcagcatgt cggtcatgtg ccacattctc | 660 |
| tggaacgacg gcgacaacac gtacaagggc aagccgctct tccgcgcggg catcatgcag | 720 |
| ctgggggcca tggtgccgct ggacgccgtg gacggcatct acggcaacga gatctttgac | 780 |

-continued

```
ctcttggcgt cgaacgcggg ctgcggcagc gccagcgaca agcttgcgtg cttgcgcggt    840
gtgctgtacg acacgttgga ggacgccacc aacaacaccc ctgggttctt ggcgtactcc    900
tcgttgcggt tgctgtacct cccccggccc gacggcgtga acatcaccga cgacatgtac    960
gccttggtgc gcgagggcaa gtatgccaac atccctgtga tcatcggcga ccagaacgac   1020
gagggcacct tctttggcac cctgctgttg aacgtgacca cggatgccca ggcccgcgag   1080
tacttcaagc agctgtttgt ccacgccagc gacgcggaga tcgacacgtt gatgacggcg   1140
taccccggcg acatcaccca gggcctgccg ttcgacacgg gtattctcaa cgccctcacc   1200
ccgcagttca agagaatcct ggcggtgctc ggcgaccttg gtttacgct tgctcgtcgc    1260
tacttcctca accactacac cggcggcacc aagtactcat tcctcctgaa gcagctcctg   1320
ggcttgccgg tgctcggaac gttccactcc aacgacattg tcttccagga ctacttgttg   1380
ggcagcggct cgctcatcta caacaacgcg ttcattgcgt ttgccacgga cttggacccc   1440
aacaccgcgg ggttgttggt gaagtggccc gagtacacca gcagcctgca gctgggcaac   1500
aacttgatga tgatcaacgc cttgggcttg tacaccggca aggacaactt ccgcaccgcc   1560
ggctacgacg cgttgttctc caacccgccg ctgttctttg tgtga                   1605
```

<210> SEQ ID NO 13
<211> LENGTH: 1605
<212> TYPE: DNA
<213> ORGANISM: Artificial Sequence
<220> FEATURE:
<223> OTHER INFORMATION: Mutant enzyme 6(S300P)

<400> SEQUENCE: 13

```
gcccccaccg ccacgctcgc caacggcgac accatcaccg gtctcaacgc catcatcaac     60
gaggcgttcc tcggcattcc ctttgccgag ccgccggtgg gcaacctccg cttcaaggac    120
cccgtgccgt actccggctc gctcgatggc cagaagttca cgctgtacgg cccgctgtgc    180
atgcagcaga accccgaggg cacctacgag gagaacctcc ccaaggcagc gctcgacttg    240
gtgatgcagt ccaaggtgtt tgaggcggtg ctgccgctga gcgaggactg tctcaccatc    300
aacgtggtgc ggccgccggg caccaaggcg ggtgccaacc tcccggtgat gctctggatc    360
tttggcggcg ggtttgaggt gggtggcacc agcaccttcc ctcccgccca gatgatcacc    420
aagagcattg ccatgggcaa gcccatcatc acgtgagcg tcaactaccg cgtgtcgtcg    480
tgggggttct tggctggcga cgagatcaag gccgagggca gtgccaacgc cggtttgaag    540
gaccagcgct gggcatgca gtgggtggcg gacaacattg cggcgtttgg cggcgacccg    600
accaaggtga ccatctttgg cgagctggcg ggcagcatgt cggtcatgtg ccacattctc    660
tggaacgacg gcgacaacac gtacaagggc aagccgctct ccgcgcgggg catcatgcag    720
ctgggggcca tggtgccgct ggacgccgtg gacggcatct acggcaacga gatctttgac    780
ctcttggcgt cgaacgcggg ctgcggcagc gccagcgaca agcttgcgtg cttgcgcggt    840
gtgctgagcg acacgttgga ggacgccacc aacaacaccc ctgggttctt ggcgtacccg    900
tcgttgcggt tgctgtacct cccccggccc gacggcgtga acatcaccga cgacatgtac    960
gccttggtgc gcgagggcaa gtatgccaac atccctgtga tcatcggcga ccagaacgac   1020
gagggcacct tctttggcac cctgctgttg aacgtgacca cggatgccca ggcccgcgag   1080
tacttcaagc agctgtttgt ccacgccagc gacgcggaga tcgacacgtt gatgacggcg   1140
taccccggcg acatcaccca gggcctgccg ttcgacacgg gtattctcaa cgccctcacc   1200
```

```
ccgcagttca agagaatcct ggcggtgctc ggcgaccttg gctttacgct tgctcgtcgc   1260
tacttcctca accactacac cggcggcacc aagtactcat tcctcctgaa gcagctcctg   1320
ggcttgccgg tgctcggaac gttccactcc aacgacattg tcttccagga ctacttgttg   1380
ggcagcggct cgctcatcta caacaacgcg ttcattgcgt ttgccacgga cttggacccc   1440
aacaccgcgg ggttgttggt gaagtggccc gagtacacca gcagcctgca gctgggcaac   1500
aacttgatga tgatcaacgc cttgggcttg tacaccggca aggacaactt ccgcaccgcc   1560
ggctacgacg cgttgttctc caacccgccg ctgttctttg tgtga                  1605
```

<210> SEQ ID NO 14
<211> LENGTH: 1605
<212> TYPE: DNA
<213> ORGANISM: Artificial Sequence
<220> FEATURE:
<223> OTHER INFORMATION: Mutant enzyme 1(T130C-S153C)

<400> SEQUENCE: 14

```
gcaccaactg caaccttagc aaacggagac acaatcactg gtttgaacgc cattatcaac     60
gaagccttct tgggaatccc atttgccgaa ccacctgtcg gaaacttgag gttcaaggac    120
ccagtacctt actcaggttc attggacggt cagaaattca cctcttacgg tccatcttgt    180
atgcaacaga atcctgaggg aacctatgag gagaacttgc caaaagcagc tttggatttg    240
gtcatgcagt caaaagtctt cgaggccgtc tcaccatctt ctgaggactg tttgacaatt    300
aacgtcgtta ggcctcctgg aaccaaagcc ggtgctaatt tgcctgtcat gttatggatc    360
ttcggaggag gttttgaagt tggaggttgt tctacatttc cacctgccca gatgatcaca    420
aaatctatcg ccatgggaaa gcctattatc cacgtatgtg tcaactatag ggtttcatct    480
tggggttttt tagctggaga cgaaatcaag gctgaaggat cagcaaatgc aggtttaaag    540
gaccagagat taggaatgca atgggttgcc gacaatatag cagcctttgg tggagaccct    600
acaaaggtta ccattttcgg agaatctgct ggatctatgt cagtcatgtg ccacatattg    660
tggaacgatg agacaacac  ctacaagggt aaaccattgt tcagagcagg tattatgcaa    720
tcaggtgcca tggttccttc tgatgctgtt gacggtatct acggaaacga ttttcgac     780 ttattagctt ctaacgccgg atgcggatct gcctcagata agttggcatg tttaagggga    840
gtctcttcag ataccttgga ggatgccacc aacaacacac caggattttt ggcctattct    900
tctttgagat tgtcatactt gcctagacca gacggagtca atattactga cgacatgtac    960
gcattagtca gagagggaaa gtacgcaaac atcccagtca taattggaga tcagaacgac   1020
gagggtacat tcttcggtac ctcatcattg aacgttacaa cagatgctca agcaagggag   1080
tatttcaaac aatcatttgt tcacgcatct gacgccgaaa tagacacttt aatgaccgcc   1140
tacccaggtg acataaccca gggttcacca ttcgatactg gtatcttaaa cgcttttgaca   1200 cctcagttta aaggatatc  agctgttttt ggtgacttag gattcacatt agctagaaga   1260
tacttcttga atcactacac tggtggtaca agtattctt  tcttgtctaa gcaattatca   1320 ggttttgccag ttttaggaac cttccactct aatgacattg tcttccaaga ctacttgttg   1380
ggatctggat cattaatcta caataacgca ttcatcgcct ttgccacaga tttggacccct   1440 aacacagcag gattgttagt aaagtggcct gaatacacat catcttcaca gtctggaaac   1500
aatttgatga tgattaacgc cttaggtttg tacaccggta agataacctt taggacagct   1560
ggttacgacg ccttgttctc taacccacct tcattttttcg tatga                   1605
```

<210> SEQ ID NO 15
<211> LENGTH: 1605
<212> TYPE: DNA
<213> ORGANISM: Artificial Sequence
<220> FEATURE:
<223> OTHER INFORMATION: Mutant enzyme 2(A249P)

<400> SEQUENCE: 15

| | |
|---|---|
| gcaccaactg caaccttagc aaacggagac acaatcactg gtttgaacgc cattatcaac | 60 |
| gaagccttct tgggaatccc atttgccgaa ccacctgtcg gaaacttgag gttcaaggac | 120 |
| ccagtacctt actcaggttc attggacggt cagaaattca cctcttacgg tccatcttgt | 180 |
| atgcaacaga atcctgaggg aacctatgag agaaacttgc caaagcagc tttggatttg | 240 |
| gtcatgcagt caaaagtctt cgaggccgtc tcaccatctt ctgaggactg tttgacaatt | 300 |
| aacgtcgtta ggcctcctgg aaccaaagcc ggtgctaatt tgcctgtcat gttatggatc | 360 |
| ttcggaggag gttttgaagt tggaggtaca tctacatttc cacctgccca gatgatcaca | 420 |
| aaatctatcg ccatgggaaa gcctattatc cacgtatcag tcaactatag ggtttcatct | 480 |
| tggggttttt tagctggaga cgaaatcaag gctgaaggat cagcaaatgc aggtttaaag | 540 |
| gaccagagat taggaatgca atgggttgcc gacaatatag cagcctttgg tggagaccct | 600 |
| acaaaggtta ccattttcgg agaatctgct ggatctatgt cagtcatgtg ccacatattg | 660 |
| tggaacgatg gagacaacac ctacaagggt aaaccattgt tcagagcagg tattatgcaa | 720 |
| tcaggtgcca tggttccttc tgatccggtt gacggtatct acggaaacga gattttcgac | 780 |
| ttattagctt ctaacgccgg atgcggatct gcctcagata agttggcatg tttaagggga | 840 |
| gtctcttcag ataccttgga ggatgccacc aacaacacac aggattttt ggcctattct | 900 |
| tctttgagat tgtcatactt gcctagacca gacggagtca atattactga cgacatgtac | 960 |
| gcattagtca gagagggaaa gtacgcaaac atcccagtca taattggaga tcagaacgac | 1020 |
| gagggtacat tcttcggtac ctcatcattg aacgttacaa cagatgctca agcaagggag | 1080 |
| tatttcaaac aatcatttgt tcacgcatct gacgccgaaa tagacacttt aatgaccgcc | 1140 |
| tacccaggtg acataaccca gggttcacca ttcgatactg gtatcttaaa cgctttgaca | 1200 |
| cctcagttta aaggatatc agctgttttg ggtgacttag gattcacatt agctagaaga | 1260 |
| tacttcttga atcactacac tggtggtaca aagtattctt tcttgtctaa gcaattatca | 1320 |
| ggtttgccag tttaggaac cttccactct aatgacattg tcttccaaga ctacttgttg | 1380 |
| ggatctggat cattaatcta caataacgca ttcatcgcct tgccacaga tttggaccct | 1440 |
| aacacagcag gattgttagt aaagtggcct gaatacacat catcttcaca gtctggaaac | 1500 |
| aatttgatga tgattaacgc cttaggtttg tacaccggta agataactt taggacagct | 1560 |
| ggttacgacg ccttgttctc taacccacct tcattttcg tatga | 1605 |

<210> SEQ ID NO 16
<211> LENGTH: 1605
<212> TYPE: DNA
<213> ORGANISM: Artificial Sequence
<220> FEATURE:
<223> OTHER INFORMATION: Mutant enzyme 3(F259Y)

<400> SEQUENCE: 16

| | |
|---|---|
| gcaccaactg caaccttagc aaacggagac acaatcactg gtttgaacgc cattatcaac | 60 |
| gaagccttct tgggaatccc atttgccgaa ccacctgtcg gaaacttgag gttcaaggac | 120 |
| ccagtacctt actcaggttc attggacggt cagaaattca cctcttacgg tccatcttgt | 180 |

```
atgcaacaga atcctgaggg aacctatgag gagaacttgc caaaagcagc tttggatttg    240
gtcatgcagt caaaagtctt cgaggccgtc tcaccatctt ctgaggactg tttgacaatt    300
aacgtcgtta ggcctcctgg aaccaaagcc ggtgctaatt tgcctgtcat gttatggatc    360
ttcggaggag gttttgaagt tggaggtaca tctacatttc cacctgccca gatgatcaca    420
aaatctatcg ccatgggaaa gcctattatc cacgtatcag tcaactatag ggtttcatct    480 tgggggttttt tagctggaga cgaaatcaag gctgaaggat cagcaaatgc aggtttaaag    540
gaccagagat taggaatgca atgggttgcc gacaatatag cagcctttgg tggagaccct    600
acaaaggtta ccattttcgg agaatctgct ggatctatgt cagtcatgtg ccacatattg    660
tggaacgatg agacaacac ctacaagggt aaaccattgt tcagagcagg tattatgcaa    720
tcaggtgcca tggttccttc tgatgctgtt gacggtatcc acggaaacga gatttacgac    780
ttattagctt ctaacgccgg atgcggatct gcctcagata agttggcatg tttaagggga    840
gtctcttcag ataccttgga ggatgccacc aacaacacac caggattttt ggcctattct    900
tctttgagat tgtcatactt gcctagacca gacgagtca atattactga cgacatgtac    960
gcattagtca gagagggaaa gtacgcaaac atcccagtca taattggaga tcagaacgac    1020
gagggtacat tcttcggtac ctcatcattg aacgttacaa cagatgctca agcaaggag    1080 tatttcaaac aatcatttgt tcacgcatct gacgccgaaa tagacacttt aatgaccgcc    1140
tacccaggtg acataaccca gggttcacca ttcgatactg gtatcttaaa cgctttgaca    1200
cctcagttta aaggatatc agctgttttg ggtgacttag gattcacatt agctagaaga    1260
tacttcttga atcactacac tggtggtaca agtattcttt cttgtctaa gcaattatca    1320 ggtttgccag ttttaggaac cttccactct aatgacattg tcttccaaga ctacttgttg    1380
ggatctggat cattaatcta caataacgca ttcatcgcct tgccacagaa tttggaccct    1440
aacacagcag gattgttagt aaagtggcct gaatacacat catcttcaca gtctggaaac    1500
aatttgatga tgattaacgc cttaggtttg tacaccggta aagataactt taggacagct    1560
ggttacgacg ccttgttctc taacccacct tcattttcg tatga              1605
```

<210> SEQ ID NO 17
<211> LENGTH: 1605
<212> TYPE: DNA
<213> ORGANISM: Artificial Sequence
<220> FEATURE:
<223> OTHER INFORMATION: Mutant enzyme 4(S282P)

<400> SEQUENCE: 17

```
gcaccaactg caaccttagc aaacggagac acaatcactg gtttgaacgc cattatcaac     60
gaagccttct tgggaatccc atttgccgaa ccacctgtcg gaaacttgag gttcaaggac    120
ccagtacctt actcaggttc attggacggt cagaaattca cctcttacgg tccatcttgt    180
atgcaacaga atcctgaggg aacctatgag gagaacttgc caaaagcagc tttggatttg    240
gtcatgcagt caaaagtctt cgaggccgtc tcaccatctt ctgaggactg tttgacaatt    300
aacgtcgtta ggcctcctgg aaccaaagcc ggtgctaatt tgcctgtcat gttatggatc    360
ttcggaggag gttttgaagt tggaggtaca tctacatttc cacctgccca gatgatcaca    420
aaatctatcg ccatgggaaa gcctattatc cacgtatcag tcaactatag ggtttcatct    480 tgggggttttt tagctggaga cgaaatcaag gctgaaggat cagcaaatgc aggtttaaag    540
gaccagagat taggaatgca atgggttgcc gacaatatag cagcctttgg tggagaccct    600
acaaaggtta ccattttcgg agaatctgct ggatctatgt cagtcatgtg ccacatattg    660
```

```
tggaacgatg agacaacac ctacaagggt aaaccattgt tcagagcagg tattatgcaa    720
tcaggtgcca tggttccttc tgatgctgtt gacggtatct acggaaacga gattttcgac    780
ttattagctt ctaacgccgg atgcggatct gcctcagata agttggcatg tttaagggga    840
gtcccgtcag ataccttgga ggatgccacc aacaacacac caggattttt ggcctattct    900
tctttgagat tgtcatactt gcctagacca gacggagtca atattactga cgacatgtac    960
gcattagtca gagagggaaa gtacgcaaac atcccagtca taattggaga tcagaacgac   1020
gagggtacat tcttcggtac ctcatcattg aacgttacaa cagatgctca agcaagggag   1080
tatttcaaac aatcatttgt tcacgcatct gacgccgaaa tagacacttt aatgaccgcc   1140
tacccaggtg acataaccca gggttcacca ttcgatactg gtatcttaaa cgctttgaca   1200
cctcagttta aaaggatatc agctgttttg ggtgacttag gattcacatt agctagaaga   1260
tacttcttga atcactacac tggtggtaca aagtattctt tcttgtctaa gcaattatca   1320
ggtttgccag ttttaggaac cttccactct aatgacattg tcttccaaga ctacttgttg   1380
ggatctggat cattaatcta caataacgca ttcatcgcct ttgccacaga tttggaccct   1440
aacacagcag gattgttagt aaagtggcct gaatacacat catcttcaca gtctggaaac   1500
aatttgatga tgattaacgc cttaggtttg tacaccggta agataaactt taggacagct   1560
ggttacgacg ccttgttctc taacccacct tcattttttcg tatga                 1605

<210> SEQ ID NO 18
<211> LENGTH: 1605
<212> TYPE: DNA
<213> ORGANISM: Artificial Sequence
<220> FEATURE:
<223> OTHER INFORMATION: Mutant enzyme 5(S283Y)

<400> SEQUENCE: 18
gcaccaactg caaccttagc aaacggagac acaatcactg gtttgaacgc cattatcaac     60
gaagccttct tgggaatccc atttgccgaa ccacctgtcg gaaacttgag gttcaaggac    120
ccagtacctt actcaggttc attggacggt cagaaattca cctcttacgg tccatcttgt    180
atgcaacaga atcctgaggg aacctatgag gagaacttgc caaaagcagc tttggatttg    240
gtcatgcagt caaaagtctt cgaggccgtc tcaccatctt ctgaggactg tttgacaatt    300
aacgtcgtta ggcctcctgg aaccaaagcc ggtgctaatt tgcctgtcat gttatggatc    360
ttcggaggag gttttgaagt tggaggtaca tctacattt cacctgccca gatgatcaca    420
aaatctatcg ccatgggaaa gcctattatc cacgtatcag tcaactatag ggtttcatct    480 tgggttttt tagctggaga cgaaatcaag gctgaaggat cagcaaatgc aggtttaaag    540
gaccagagat taggaatgca atgggttgcc gacaatatag cagcctttgg tggagaccct    600
acaaaggtta ccatttcgg agaatctgct ggatctatgt cagtcatgtg ccacatattg    660
tggaacgatg agacaacac ctacaagggt aaaccattgt tcagagcagg tattatgcaa    720
tcaggtgcca tggttccttc tgatgctgtt gacggtatct acggaaacga gattttcgac    780
ttattagctt ctaacgccgg atgcggatct gcctcagata agttggcatg tttaagggga    840
gtctcttacg ataccttgga ggatgccacc aacaacacac caggattttt ggcctattct    900
tctttgagat tgtcatactt gcctagacca gacggagtca atattactga cgacatgtac    960
gcattagtca gagagggaaa gtacgcaaac atcccagtca taattggaga tcagaacgac   1020
gagggtacat tcttcggtac ctcatcattg aacgttacaa cagatgctca agcaagggag   1080
```

```
tatttcaaac aatcatttgt tcacgcatct gacgccgaaa tagacacttt aatgaccgcc    1140
tacccaggtg acataaccca gggttcacca ttcgatactg gtatcttaaa cgctttgaca    1200
cctcagttta aaggatatc agctgttttg ggtgacttag gattcacatt agctagaaga    1260
tacttcttga atcactacac tggtggtaca aagtattctt tcttgtctaa gcaattatca    1320
ggtttgccag ttttaggaac cttccactct aatgacattg tcttccaaga ctacttgttg    1380
ggatctggat cattaatcta caataacgca ttcatcgcct tgccacaga tttggaccct     1440 aacacagcag gattgttagt aaagtggcct gaatacacat catcttcaca gtctggaaac    1500
aatttgatga tgattaacgc cttaggtttg tacaccggta agataacctt taggacagct    1560
ggttacgacg ccttgttctc taacccacct tcattttcg tatga                    1605
```

<210> SEQ ID NO 19
<211> LENGTH: 1605
<212> TYPE: DNA
<213> ORGANISM: Artificial Sequence
<220> FEATURE:
<223> OTHER INFORMATION: Mutant enzyme 6(S300P)

<400> SEQUENCE: 19

```
gcaccaactg caaccttagc aaacggagac acaatcactg gtttgaacgc cattatcaac     60
gaagccttct tgggaatccc atttgccgaa ccacctgtcg gaaacttgag gttcaaggac    120
ccagtacctt actcaggttc attggacggt cagaaattca cctcttacgg tccatcttgt    180
atgcaacaga tcctgaggg aacctatgag gagaacttgc caaaagcagc tttggatttg    240
gtcatgcagt caaaagtctt cgaggccgtc tcaccatctt ctgaggactg tttgacaatt    300
aacgtcgtta ggcctcctgg aaccaaagcc ggtgctaatt tgcctgtcat gttatggatc    360
ttcggaggag gttttgaagt tggaggtaca tctacatttc cacctgccca gatgatcaca    420
aaatctatcg ccatgggaaa gccttattatc cacgtatcag tcaactatag ggtttcatct    480
tggggttttt tagctggaga cgaaatcaag gctgaaggat cagcaaatgc aggtttaaag    540
gaccagagat taggaatgca atgggttgcc gacaatatag cagccttgg tggagaccct    600 acaaaggtta ccatttcgg agaatctgct ggatctatgt cagtcatgtg ccacatattg    660
tggaacgatg gagacaacac ctacaagggt aaaccattgt tcagagcagg tattatgcaa    720
tcaggtgcca tggttccttc tgatgctgtt gacggtatct acggaaacga gatttttcgac    780 ttattagctt ctaacgccgg atgcggatct gcctcagata agttggcatg tttaaggga    840 gtctcttcag ataccttgga ggatgccacc aacaacacac aggattttt ggcctatccg     900 tctttgagat tgtcatactt gcctagacca gacggagtca atattactga cgacatgtac    960
gcattagtca gagagggaaa gtacgcaaac atcccagtca taattggaga tcagaacgac    1020
gagggtacat tcttcggtac ctcatcattg aacgttacaa cagatgctca agcaagggag    1080
tatttcaaac aatcatttgt tcacgcatct gacgccgaaa tagacacttt aatgaccgcc    1140
tacccaggtg acataaccca gggttcacca ttcgatactg gtatcttaaa cgctttgaca    1200
cctcagttta aaggatatc agctgttttg ggtgacttag gattcacatt agctagaaga    1260
tacttcttga atcactacac tggtggtaca aagtattctt tcttgtctaa gcaattatca    1320
ggtttgccag ttttaggaac cttccactct aatgacattg tcttccaaga ctacttgttg    1380
ggatctggat cattaatcta caataacgca ttcatcgcct tgccacaga tttggaccct     1440 aacacagcag gattgttagt aaagtggcct gaatacacat catcttcaca gtctggaaac    1500
aatttgatga tgattaacgc cttaggtttg tacaccggta agataacctt taggacagct    1560
```

```
ggttacgacg ccttgttctc taacccacct tcattttcg tatga                    1605
```

<210> SEQ ID NO 20
<211> LENGTH: 45
<212> TYPE: DNA
<213> ORGANISM: Candida cylindracea

<400> SEQUENCE: 20

```
atggagctcg ctcttgcgct cctgctcatt gcctcggtgg ctgct                    45
```

<210> SEQ ID NO 21
<211> LENGTH: 15
<212> TYPE: PRT
<213> ORGANISM: Candida cylindracea

<400> SEQUENCE: 21

```
Met Glu Leu Ala Leu Ala Leu Ser Leu Ile Ala Ser Val Ala Ala
1               5                   10                  15
```

<210> SEQ ID NO 22
<211> LENGTH: 549
<212> TYPE: PRT
<213> ORGANISM: Candida cylindracea

<400> SEQUENCE: 22

```
Met Glu Leu Ala Leu Ala Leu Ser Leu Ile Ala Ser Val Ala Ala
1               5                   10                  15

Pro Thr Ala Thr Leu Ala Asn Gly Asp Thr Ile Thr Gly Leu Asn Ala
            20                  25                  30

Ile Ile Asn Glu Ala Phe Leu Gly Ile Pro Phe Ala Glu Pro Pro Val
        35                  40                  45

Gly Asn Leu Arg Phe Lys Asp Pro Val Pro Tyr Ser Gly Ser Leu Asp
    50                  55                  60

Gly Gln Lys Phe Thr Ser Tyr Gly Pro Ser Cys Met Gln Gln Asn Pro
65                  70                  75                  80

Glu Gly Thr Tyr Glu Glu Asn Leu Pro Lys Ala Ala Leu Asp Leu Val
                85                  90                  95

Met Gln Ser Lys Val Phe Glu Ala Val Ser Pro Ser Ser Glu Asp Cys
            100                 105                 110

Leu Thr Ile Asn Val Val Arg Pro Pro Gly Thr Lys Ala Gly Ala Asn
        115                 120                 125

Leu Pro Val Met Leu Trp Ile Phe Gly Gly Gly Phe Glu Val Gly Gly
    130                 135                 140

Thr Ser Thr Phe Pro Pro Ala Gln Met Ile Thr Lys Ser Ile Ala Met
145                 150                 155                 160

Gly Lys Pro Ile Ile His Val Ser Val Asn Tyr Arg Val Ser Ser Trp
                165                 170                 175

Gly Phe Leu Ala Gly Asp Glu Ile Lys Ala Glu Gly Ser Ala Asn Ala
            180                 185                 190

Gly Leu Lys Asp Gln Arg Leu Gly Met Gln Trp Val Ala Asp Asn Ile
        195                 200                 205

Ala Ala Phe Gly Gly Asp Pro Thr Lys Val Thr Ile Phe Gly Glu Ser
    210                 215                 220

Ala Gly Ser Met Ser Val Met Cys His Ile Leu Trp Asn Asp Gly Asp
225                 230                 235                 240

Asn Thr Tyr Lys Gly Lys Pro Leu Phe Arg Ala Gly Ile Met Gln Ser
                245                 250                 255
```

```
Gly Ala Met Val Pro Ser Asp Ala Val Asp Gly Ile Tyr Gly Asn Glu
            260                 265                 270

Ile Phe Asp Leu Leu Ala Ser Asn Ala Gly Cys Gly Ser Ala Ser Asp
        275                 280                 285

Lys Leu Ala Cys Leu Arg Gly Val Ser Ser Asp Thr Leu Glu Asp Ala
    290                 295                 300

Thr Asn Asn Thr Pro Gly Phe Leu Ala Tyr Ser Ser Leu Arg Leu Ser
305                 310                 315                 320

Tyr Leu Pro Arg Pro Asp Gly Val Asn Ile Thr Asp Met Tyr Ala
                325                 330                 335

Leu Val Arg Glu Gly Lys Tyr Ala Asn Ile Pro Val Ile Gly Asp
            340                 345                 350

Gln Asn Asp Glu Gly Thr Phe Phe Gly Thr Ser Ser Leu Asn Val Thr
        355                 360                 365

Thr Asp Ala Gln Ala Arg Glu Tyr Phe Lys Gln Ser Phe Val His Ala
    370                 375                 380

Ser Asp Ala Glu Ile Asp Thr Leu Met Thr Ala Tyr Pro Gly Asp Ile
385                 390                 395                 400

Thr Gln Gly Ser Pro Phe Asp Thr Gly Ile Leu Asn Ala Leu Thr Pro
                405                 410                 415

Gln Phe Lys Arg Ile Ser Ala Val Leu Gly Asp Leu Gly Phe Thr Leu
            420                 425                 430

Ala Arg Arg Tyr Phe Leu Asn His Tyr Thr Gly Gly Thr Lys Tyr Ser
        435                 440                 445

Phe Leu Ser Lys Gln Leu Ser Gly Leu Pro Val Leu Gly Thr Phe His
    450                 455                 460

Ser Asn Asp Ile Val Phe Gln Asp Tyr Leu Leu Gly Ser Gly Ser Leu
465                 470                 475                 480

Ile Tyr Asn Asn Ala Phe Ile Ala Phe Ala Thr Asp Leu Asp Pro Asn
                485                 490                 495

Thr Ala Gly Leu Leu Val Lys Trp Pro Glu Tyr Thr Ser Ser Ser Gln
            500                 505                 510

Ser Gly Asn Asn Leu Met Met Ile Asn Ala Leu Gly Leu Tyr Thr Gly
        515                 520                 525

Lys Asp Asn Phe Arg Thr Ala Gly Tyr Asp Ala Leu Phe Ser Asn Pro
    530                 535                 540

Pro Ser Phe Phe Val
545
```

<210> SEQ ID NO 23
<211> LENGTH: 1650
<212> TYPE: DNA
<213> ORGANISM: Candida cylindracea

<400> SEQUENCE: 23

```
atggagctcg ctcttgcgct cctgctcatt gcctcggtgg ctgctgcccc caccgccacg      60
ctcgccaacg gcgacaccat caccggtctc aacgccatca tcaacgaggc gttcctcggc     120 attcccttttg ccgagccgcc ggtgggcaac ctccgcttca aggaccccgt gccgtactcc     180
ggctcgctcg atggccagaa gttcacgctg tacggcccgc tgtgcatgca gcagaacccc     240
gagggcacct acgaggagaa cctcccccaag gcagcgctcg acttggtgat gcagtccaag     300
gtgtttgagg cggtgctgcc gctgagcgag actgtctca ccatcaacgt ggtgcggccg      360
ccgggcacca aggcgggtgc caacctcccg gtgatgctct ggatctttgg cggcgggttt     420
```

```
gaggtgggtg gcaccagcac cttccctccc gcccagatga tcaccaagag cattgccatg    480
ggcaagccca tcatccacgt gagcgtcaac taccgcgtgt cgtcgtgggg gttcttggct    540
ggcgacgaga tcaaggccga gggcagtgcc aacgccggtt tgaaggacca gcgcttgggc    600
atgcagtggg tggcggacaa cattgcggcg tttggcggcg acccgaccaa ggtgaccatc    660
tttggcgagc tggcgggcag catgtcggtc atgtgccaca ttctctggaa cgacggcgac    720
aacacgtaca agggcaagcc gctcttccgc gcgggcatca tgcagctggg ggccatggtg    780
ccgctggacg ccgtggacgg catctacggc aacgagatct ttgacctctt ggcgtcgaac    840
gcgggctgcg gcagcgccag cgacaagctt gcgtgcttgc gcggtgtgct gagcgacacg    900
ttggaggacg ccaccaacaa caccccgggg ttcttggcgt actcctcgtt gcggttgctg    960
tacctccccc ggcccgacgg cgtgaacatc accgacgaca tgtacgcctt ggtgcgcgag   1020
ggcaagtatg ccaacatccc tgtgatcatc ggcgaccaga cgacgagggg caccttcttt   1080 ggcacccctgc tgttgaacgt gaccacggat gcccaggccc gcgagtactt caagcagctg   1140
tttgtccacg ccagcgacgc ggagatcgac acgttgatga cggcgtaccc cggcgacatc   1200
acccagggcc tgccgttcga cacgggtatt ctcaacgccc tcaccccgca gttcaagaga   1260
atcctggcgg tgctcggcga ccttggcttt acgcttgctc gtcgctactt cctcaaccac   1320
tacaccggcg gcaccaagta ctcattcctc ctgaagcagc tcctgggctt gccggtgctc   1380
ggaacgttcc actccaacga cattgtcttc caggactact tgttgggcag cggctcgctc   1440
atctacaaca acgcgttcat tgcgtttgcc acggacttgg accccaacac cgcggggttg   1500
ttggtgaagt ggcccgagta caccagcagc ctgcagctgg gcaacaactt gatgatgatc   1560
aacgccttgg gcttgtacac cggcaaggac aacttccgca ccgccggcta cgacgcgttg   1620
ttctccaacc cgccgctgtt ctttgtgtga                                     1650
```

<210> SEQ ID NO 24
<211> LENGTH: 534
<212> TYPE: PRT
<213> ORGANISM: Candida cylindracea

<400> SEQUENCE: 24

```
Ala Pro Thr Ala Thr Leu Ala Asn Gly Asp Thr Ile Thr Gly Leu Asn
1               5                   10                  15

Ala Ile Val Asn Glu Lys Phe Leu Gly Ile Pro Phe Ala Glu Pro Pro
                20                  25                  30

Val Gly Thr Leu Arg Phe Lys Pro Pro Val Pro Tyr Ser Ala Ser Leu
            35                  40                  45

Asn Gly Gln Gln Phe Thr Ser Tyr Gly Pro Ser Cys Met Gln Met Asn
        50                  55                  60

Pro Met Gly Ser Phe Glu Asp Thr Leu Pro Lys Asn Ala Arg His Leu
65                  70                  75                  80

Val Leu Gln Ser Lys Ile Phe Gln Val Val Leu Pro Asn Asp Glu Asp
                85                  90                  95

Cys Leu Thr Ile Asn Val Ile Arg Pro Pro Gly Thr Arg Ala Ser Ala
            100                 105                 110

Gly Leu Pro Val Met Leu Trp Ile Phe Gly Gly Phe Glu Leu Gly
            115                 120                 125

Gly Ser Ser Leu Phe Pro Gly Asp Gln Met Val Ala Lys Ser Val Leu
        130                 135                 140

Met Gly Lys Pro Val Ile His Val Ser Met Asn Tyr Arg Val Ala Ser
```

```
                145                 150                 155                 160
        Trp Gly Phe Leu Ala Gly Pro Asp Ile Gln Asn Glu Gly Ser Gly Asn
                        165                 170                 175

Ala Gly Leu His Asp Gln Arg Leu Ala Met Gln Trp Val Ala Asp Asn
                    180                 185                 190

Ile Ala Gly Phe Gly Gly Asp Pro Ser Lys Val Thr Ile Tyr Gly Glu
                    195                 200                 205

Ser Ala Gly Ser Met Ser Thr Phe Val His Leu Val Trp Asn Asp Gly
                    210                 215                 220

Asp Asn Thr Tyr Asn Gly Lys Pro Leu Phe Arg Ala Ile Met Gln
        225                 230                 235                 240

Ser Gly Cys Met Val Pro Ser Asp Pro Val Asp Gly Thr Tyr Gly Thr
                            245                 250                 255

Glu Ile Tyr Asn Gln Val Val Ser Ala Gly Cys Gly Ser Ala Ser
                        260                 265                 270

Asp Lys Leu Ala Cys Leu Arg Gly Leu Ser Gln Asp Thr Leu Tyr Gln
                        275                 280                 285

Ala Thr Ser Asp Thr Pro Gly Val Leu Ala Tyr Pro Ser Leu Arg Leu
                    290                 295                 300

Ser Tyr Leu Pro Arg Pro Asp Gly Thr Phe Ile Thr Asp Met Tyr
        305                 310                 315                 320

Ala Leu Val Arg Asp Gly Lys Tyr Ala His Val Pro Val Ile Ile Gly
                            325                 330                 335

Asp Gln Asn Asp Glu Gly Thr Leu Phe Gly Leu Ser Ser Leu Asn Val
                        340                 345                 350

Thr Thr Asp Ala Gln Ala Arg Ala Tyr Phe Lys Gln Ser Phe Ile His
                    355                 360                 365

Ala Ser Asp Ala Glu Ile Asp Thr Leu Met Ala Ala Tyr Thr Ser Asp
                    370                 375                 380

Ile Thr Gln Gly Ser Pro Phe Asp Thr Gly Ile Phe Asn Ala Ile Thr
        385                 390                 395                 400

Pro Gln Phe Lys Arg Ile Ser Ala Leu Leu Gly Asp Leu Ala Phe Thr
                        405                 410                 415

Leu Ala Arg Arg Tyr Phe Leu Asn Tyr Tyr Gln Gly Thr Lys Tyr
                        420                 425                 430

Ser Phe Leu Ser Lys Gln Leu Ser Gly Leu Pro Val Leu Gly Thr Phe
                    435                 440                 445

His Gly Asn Asp Ile Ile Trp Gln Asp Tyr Leu Val Gly Ser Gly Ser
                    450                 455                 460

Val Ile Tyr Asn Asn Ala Phe Ile Ala Phe Ala Asn Asp Leu Asp Pro
        465                 470                 475                 480

Asn Lys Ala Gly Leu Trp Thr Asn Trp Pro Thr Tyr Thr Ser Ser
                        485                 490                 495

Gln Ser Gly Asn Asn Leu Met Gln Ile Asn Gly Leu Gly Leu Tyr Thr
                    500                 505                 510

Gly Lys Asp Asn Phe Arg Pro Asp Ala Tyr Ser Ala Leu Phe Ser Asn
                    515                 520                 525

Pro Pro Ser Phe Phe Val
                530

<210> SEQ ID NO 25
<211> LENGTH: 534
<212> TYPE: PRT
<213> ORGANISM: Candida cylindracea
```

<400> SEQUENCE: 25

Ala Pro Thr Ala Lys Leu Ala Asn Gly Asp Thr Ile Thr Gly Leu Asn
1               5                   10                  15

Ala Ile Ile Asn Glu Ala Phe Leu Gly Ile Pro Phe Ala Glu Pro Pro
            20                  25                  30

Val Gly Asn Leu Arg Phe Lys Asp Pro Val Pro Tyr Ser Gly Ser Leu
        35                  40                  45

Asn Gly Gln Lys Phe Thr Ser Tyr Gly Pro Ser Cys Met Gln Gln Asn
    50                  55                  60

Pro Glu Gly Thr Phe Glu Glu Asn Leu Gly Lys Thr Ala Leu Asp Leu
65                  70                  75                  80

Val Met Gln Ser Lys Val Phe Gln Ala Val Leu Pro Gln Ser Glu Asp
                85                  90                  95

Cys Leu Thr Ile Asn Val Val Arg Pro Pro Gly Thr Lys Ala Gly Ala
            100                 105                 110

Asn Leu Pro Val Met Leu Trp Ile Phe Gly Gly Phe Glu Ile Gly
        115                 120                 125

Ser Pro Thr Ile Phe Pro Pro Ala Gln Met Val Thr Lys Ser Val Leu
    130                 135                 140

Met Gly Lys Pro Ile Ile His Val Ala Val Asn Tyr Arg Val Ala Ser
145                 150                 155                 160

Trp Gly Phe Leu Ala Gly Asp Asp Ile Lys Ala Glu Gly Ser Gly Asn
                165                 170                 175

Ala Gly Leu Lys Asp Gln Arg Leu Gly Met Gln Trp Val Ala Asp Asn
            180                 185                 190

Ile Ala Gly Phe Gly Gly Asp Pro Ser Lys Val Thr Ile Phe Gly Glu
        195                 200                 205

Ser Ala Gly Ser Met Ser Val Leu Cys His Leu Ile Trp Asn Asp Gly
    210                 215                 220

Asp Asn Thr Tyr Lys Gly Lys Pro Leu Phe Arg Ala Gly Ile Met Gln
225                 230                 235                 240

Ser Gly Ala Met Val Pro Ser Asp Pro Val Asp Gly Thr Tyr Gly Asn
                245                 250                 255

Glu Ile Tyr Asp Leu Phe Val Ser Ser Ala Gly Cys Gly Ser Ala Ser
            260                 265                 270

Asp Lys Leu Ala Cys Leu Arg Ser Ala Ser Ser Asp Thr Leu Leu Asp
        275                 280                 285

Ala Thr Asn Asn Thr Pro Gly Phe Leu Ala Tyr Ser Ser Leu Arg Leu
    290                 295                 300

Ser Tyr Leu Pro Arg Pro Asp Gly Lys Asn Ile Thr Asp Asp Met Tyr
305                 310                 315                 320

Lys Leu Val Arg Asp Gly Lys Tyr Ala Ser Val Pro Val Ile Ile Gly
                325                 330                 335

Asp Gln Asn Asp Glu Gly Thr Ile Phe Gly Leu Ser Ser Leu Asn Val
            340                 345                 350

Thr Thr Asn Ala Gln Ala Arg Ala Tyr Phe Lys Gln Ser Phe Ile His
        355                 360                 365

Ala Ser Asp Ala Glu Ile Asp Thr Leu Met Ala Ala Tyr Pro Gln Asp
    370                 375                 380

Ile Thr Gln Gly Ser Pro Phe Asp Thr Gly Ile Phe Asn Ala Ile Thr
385                 390                 395                 400

Pro Gln Phe Lys Arg Ile Ser Ala Val Leu Gly Asp Leu Ala Phe Ile

```
                    405                 410                 415
His Ala Arg Arg Tyr Phe Leu Asn His Phe Gln Gly Gly Thr Lys Tyr
            420                 425                 430

Ser Phe Leu Ser Lys Gln Leu Ser Gly Leu Pro Ile Met Gly Thr Phe
        435                 440                 445

His Ala Asn Asp Ile Val Trp Gln Asp Tyr Leu Leu Gly Ser Gly Ser
    450                 455                 460

Val Ile Tyr Asn Asn Ala Phe Ile Ala Phe Ala Thr Asp Leu Asp Pro
465                 470                 475                 480

Asn Thr Ala Gly Leu Leu Val Asn Trp Pro Lys Tyr Thr Ser Ser Ser
                485                 490                 495

Gln Ser Gly Asn Asn Leu Met Met Ile Asn Ala Leu Gly Leu Tyr Thr
            500                 505                 510

Gly Lys Asp Asn Phe Arg Thr Ala Gly Tyr Asp Ala Leu Met Thr Asn
        515                 520                 525

Pro Ser Ser Phe Phe Val
    530
```

<210> SEQ ID NO 26
<211> LENGTH: 534
<212> TYPE: PRT
<213> ORGANISM: Candida cylindracea

<400> SEQUENCE: 26

```
Ala Pro Thr Ala Thr Leu Ala Asn Gly Asp Thr Ile Thr Gly Leu Asn
1               5                   10                  15

Ala Ile Ile Asn Glu Ala Phe Leu Gly Ile Pro Phe Ala Gln Pro Pro
                20                  25                  30

Val Gly Asn Leu Arg Phe Lys Pro Pro Val Pro Tyr Ser Ala Ser Leu
            35                  40                  45

Asn Gly Gln Lys Phe Thr Ser Tyr Gly Pro Ser Cys Met Gln Met Asn
        50                  55                  60

Pro Leu Gly Asn Trp Asp Ser Ser Leu Pro Lys Ala Ala Ile Asn Ser
65                  70                  75                  80

Leu Met Gln Ser Lys Leu Phe Gln Ala Val Leu Pro Asn Gly Glu Asp
                85                  90                  95

Cys Leu Thr Ile Asn Val Val Arg Pro Ser Gly Thr Lys Pro Gly Ala
            100                 105                 110

Asn Leu Pro Val Met Val Trp Ile Phe Gly Gly Gly Phe Glu Val Gly
        115                 120                 125

Gly Ser Ser Leu Phe Pro Pro Ala Gln Met Ile Thr Ala Ser Val Leu
    130                 135                 140

Met Gly Lys Pro Ile Ile His Val Ser Met Asn Tyr Arg Val Ala Ser
145                 150                 155                 160

Trp Gly Phe Leu Ala Gly Pro Asp Ile Lys Ala Glu Gly Ser Gly Asn
                165                 170                 175

Ala Gly Leu His Asp Gln Arg Leu Gly Leu Gln Trp Val Ala Asp Asn
            180                 185                 190

Ile Ala Gly Phe Gly Gly Asp Pro Ser Lys Val Thr Ile Phe Gly Glu
        195                 200                 205

Ser Ala Gly Ser Met Ser Val Met Cys Gln Leu Leu Trp Asn Asp Gly
    210                 215                 220

Asp Asn Thr Tyr Asn Gly Lys Pro Leu Phe Arg Ala Ala Ile Met Gln
225                 230                 235                 240
```

-continued

Ser Gly Ala Met Val Pro Ser Asp Pro Val Asp Gly Pro Tyr Gly Thr
            245                 250                 255

Gln Ile Tyr Asp Gln Val Val Ala Ser Ala Gly Cys Gly Ser Ala Ser
        260                 265                 270

Asp Lys Leu Ala Cys Leu Arg Ser Ile Ser Asn Asp Lys Leu Phe Gln
    275                 280                 285

Ala Thr Ser Asp Thr Pro Gly Ala Leu Ala Tyr Pro Ser Leu Arg Leu
290                 295                 300

Ser Phe Leu Pro Arg Pro Asp Gly Thr Phe Ile Thr Asp Met Phe
305                 310                 315                 320

Lys Leu Val Arg Asp Gly Lys Cys Ala Asn Val Pro Val Ile Ile Gly
                325                 330                 335

Asp Gln Asn Asp Glu Gly Thr Val Phe Ala Leu Ser Ser Leu Asn Val
            340                 345                 350

Thr Thr Asp Ala Gln Ala Arg Gln Tyr Phe Lys Glu Ser Phe Ile His
        355                 360                 365

Ala Ser Asp Ala Glu Ile Asp Thr Leu Met Ala Ala Tyr Pro Ser Asp
    370                 375                 380

Ile Thr Gln Gly Ser Pro Phe Asp Thr Gly Ile Phe Asn Ala Ile Thr
385                 390                 395                 400

Pro Gln Phe Lys Arg Ile Ala Ala Val Leu Gly Asp Leu Ala Phe Thr
                405                 410                 415

Leu Pro Arg Arg Tyr Phe Leu Asn His Phe Gln Gly Gly Thr Lys Tyr
            420                 425                 430

Ser Phe Leu Ser Lys Gln Leu Ser Gly Leu Pro Val Ile Gly Thr His
        435                 440                 445

His Ala Asn Asp Ile Val Trp Gln Asp Phe Leu Val Ser His Ser Ser
    450                 455                 460

Ala Val Tyr Asn Asn Ala Phe Ile Ala Phe Ala Asn Asp Leu Asp Pro
465                 470                 475                 480

Asn Lys Ala Gly Leu Leu Val Asn Trp Pro Lys Tyr Thr Ser Ser Ser
                485                 490                 495

Gln Ser Gly Asn Asn Leu Leu Gln Ile Asn Ala Leu Gly Leu Tyr Thr
            500                 505                 510

Gly Lys Asp Asn Phe Arg Thr Ala Gly Tyr Asp Ala Leu Phe Thr Asn
        515                 520                 525

Pro Ser Ser Phe Phe Val
    530

<210> SEQ ID NO 27
<211> LENGTH: 534
<212> TYPE: PRT
<213> ORGANISM: Candida cylindracea

<400> SEQUENCE: 27

Ala Pro Thr Ala Thr Leu Ala Asn Gly Asp Thr Ile Thr Gly Leu Asn
1               5                   10                  15

Ala Ile Ile Asn Glu Ala Phe Leu Gly Ile Pro Phe Ala Glu Pro Pro
            20                  25                  30

Val Gly Asn Leu Arg Phe Lys Asp Pro Val Pro Tyr Arg Gly Ser Leu
        35                  40                  45

Asn Gly Gln Ser Phe Thr Ala Tyr Gly Pro Ser Cys Met Gln Gln Asn
    50                  55                  60

Pro Glu Gly Thr Tyr Glu Glu Asn Leu Pro Lys Val Ala Leu Asp Leu
65                  70                  75                  80

```
Val Met Gln Ser Lys Val Phe Gln Ala Val Leu Pro Asn Ser Glu Asp
                85                  90                  95

Cys Leu Thr Ile Asn Val Val Arg Pro Pro Gly Thr Lys Ala Gly Ala
                100                 105                 110

Asn Leu Pro Val Met Leu Trp Ile Phe Gly Gly Gly Phe Glu Ile Gly
                115                 120                 125

Ser Pro Thr Ile Phe Pro Pro Ala Gln Met Val Ser Lys Ser Val Leu
                130                 135                 140

Met Gly Lys Pro Ile Ile His Val Ala Val Asn Tyr Arg Leu Ala Ser
145                 150                 155                 160

Phe Gly Phe Leu Ala Gly Pro Asp Ile Lys Ala Glu Gly Ser Ser Asn
                165                 170                 175

Ala Gly Leu Lys Asp Gln Arg Leu Gly Met Gln Trp Val Ala Asp Asn
                180                 185                 190

Ile Ala Gly Phe Gly Gly Asp Pro Ser Lys Val Thr Ile Phe Gly Glu
                195                 200                 205

Ser Ala Gly Ser Met Ser Val Leu Cys His Leu Leu Trp Asn Gly Gly
                210                 215                 220

Asp Asn Thr Tyr Lys Gly Lys Pro Leu Phe Arg Ala Gly Ile Met Gln
225                 230                 235                 240

Ser Gly Ala Met Val Pro Ser Asp Pro Val Asp Gly Thr Tyr Gly Thr
                245                 250                 255

Gln Ile Tyr Asp Thr Leu Val Ala Ser Thr Gly Cys Ser Ser Ala Ser
                260                 265                 270

Asn Lys Leu Ala Cys Leu Arg Gly Leu Ser Thr Gln Ala Leu Leu Asp
                275                 280                 285

Ala Thr Asn Asp Thr Pro Gly Phe Leu Ser Tyr Thr Ser Leu Arg Leu
                290                 295                 300

Ser Tyr Leu Pro Arg Pro Asp Gly Ala Asn Ile Thr Asp Asp Met Tyr
305                 310                 315                 320

Lys Leu Val Arg Asp Gly Lys Tyr Ala Ser Val Pro Val Ile Ile Gly
                325                 330                 335

Asp Gln Asn Asp Glu Gly Phe Leu Phe Gly Leu Ser Ser Leu Asn Thr
                340                 345                 350

Thr Thr Glu Ala Asp Ala Glu Ala Tyr Leu Arg Lys Ser Phe Ile His
                355                 360                 365

Ala Thr Asp Ala Asp Ile Thr Ala Leu Lys Ala Ala Tyr Pro Ser Asp
                370                 375                 380

Val Thr Gln Gly Ser Pro Phe Asp Thr Gly Ile Leu Asn Ala Leu Thr
385                 390                 395                 400

Pro Gln Leu Lys Arg Ile Asn Ala Val Leu Gly Asp Leu Thr Phe Thr
                405                 410                 415

Leu Ser Arg Arg Tyr Phe Leu Asn His Tyr Thr Gly Gly Pro Lys Tyr
                420                 425                 430

Ser Phe Leu Ser Lys Gln Leu Ser Gly Leu Pro Ile Leu Gly Thr Phe
                435                 440                 445

His Ala Asn Asp Ile Val Trp Gln His Phe Leu Leu Gly Ser Gly Ser
                450                 455                 460

Val Ile Tyr Asn Asn Ala Phe Ile Ala Phe Ala Thr Asp Leu Asp Pro
465                 470                 475                 480

Asn Thr Ala Gly Leu Ser Val Gln Trp Pro Lys Ser Thr Ser Ser Ser
                485                 490                 495
```

```
Gln Ala Gly Asp Asn Leu Met Gln Ile Ser Ala Leu Gly Leu Tyr Thr
            500                 505                 510

Gly Lys Asp Asn Phe Arg Thr Ala Gly Tyr Asn Ala Leu Phe Ala Asp
        515                 520                 525

Pro Ser His Phe Phe Val
    530

<210> SEQ ID NO 28
<211> LENGTH: 549
<212> TYPE: PRT
<213> ORGANISM: Diutina rugosa

<400> SEQUENCE: 28

Met Glu Leu Ala Leu Ala Leu Ser Leu Ile Ala Ser Val Ala Ala Ala
1               5                   10                  15

Pro Thr Ala Thr Leu Ala Asn Gly Asp Thr Ile Thr Gly Leu Asn Ala
                20                  25                  30

Ile Ile Asn Glu Ala Phe Leu Gly Ile Pro Phe Ala Glu Pro Pro Val
            35                  40                  45

Gly Asn Leu Arg Phe Lys Asp Pro Val Pro Tyr Arg Gly Ser Leu Asn
    50                  55                  60

Gly Gln Ser Phe Thr Ala Tyr Gly Pro Ser Cys Met Gln Gln Asn Pro
65                  70                  75                  80

Glu Gly Thr Tyr Glu Glu Asn Leu Pro Lys Val Ala Leu Asp Leu Val
                85                  90                  95

Met Gln Ser Lys Val Phe Gln Ala Val Leu Ser Asn Ser Glu Asp Cys
            100                 105                 110

Leu Thr Ile Asn Val Val Arg Pro Pro Gly Thr Lys Ala Gly Ala Asn
        115                 120                 125

Leu Pro Val Met Leu Trp Ile Phe Gly Gly Gly Phe Glu Ile Gly Ser
    130                 135                 140

Pro Thr Ile Phe Pro Pro Ala Gln Met Val Ser Lys Ser Val Leu Met
145                 150                 155                 160

Gly Lys Pro Ile Ile His Val Ala Val Asn Tyr Arg Leu Ala Ser Phe
                165                 170                 175

Gly Phe Leu Ala Gly Pro Asp Ile Lys Ala Glu Gly Ser Ser Asn Ala
            180                 185                 190

Gly Leu Lys Asp Gln Arg Leu Gly Met Gln Trp Val Ala Asp Asn Ile
        195                 200                 205

Ala Gly Phe Gly Gly Asp Pro Ser Lys Val Thr Ile Phe Gly Glu Ser
    210                 215                 220

Ala Gly Ser Met Ser Val Leu Cys His Leu Leu Trp Asn Gly Gly Asp
225                 230                 235                 240

Asn Thr Tyr Lys Gly Lys Pro Leu Phe Arg Ala Gly Ile Met Gln Ser
                245                 250                 255

Gly Ala Met Val Pro Ser Asp Pro Val Asp Gly Thr Tyr Gly Thr Gln
            260                 265                 270

Ile Tyr Asp Thr Leu Val Ala Ser Thr Gly Cys Ser Ser Ala Ser Asn
        275                 280                 285

Lys Leu Ala Cys Leu Arg Gly Leu Ser Thr Gln Ala Leu Leu Asp Ala
    290                 295                 300

Thr Asn Asp Thr Pro Gly Phe Leu Ala Phe Ser Ser Leu Arg Leu Ser
305                 310                 315                 320

Tyr Leu Pro Arg Pro Asp Gly Val Asn Ile Thr Asp Asp Phe Tyr Ala
                325                 330                 335
```

```
Leu Val Arg Asn Gly Lys Tyr Ala His Val Pro Val Ile Ile Gly Asp
            340                 345                 350

Gln Asn Asp Glu Gly Thr Ile Phe Gly Leu Ser Ser Leu Asn Val Thr
        355                 360                 365

Thr Asn Ala Gln Ala Arg Glu Tyr Phe Lys Gln Ser Phe Ile His Ala
    370                 375                 380

Ser Asp Ala Glu Ile Asp Thr Leu Met Thr Ala Tyr Pro Gln Asp Ile
385                 390                 395                 400

Thr Gln Gly Ser Pro Phe Asp Thr Gly Val Leu Asn Ala Leu Thr Pro
                405                 410                 415

Gln Phe Lys Arg Ile Ser Ala Val Leu Gly Asp Leu Ala Phe Thr Leu
            420                 425                 430

Ala Arg Arg Tyr Phe Leu Asn Tyr Tyr Gln Gly Gly Thr Lys Tyr Ser
        435                 440                 445

Phe Leu Ser Lys Gln Leu Ser Gly Leu Pro Val Leu Gly Thr Phe His
    450                 455                 460

Ser Asn Asp Leu Thr Phe Gln Asn Asp Leu Leu Gly Ser Gly Ser Leu
465                 470                 475                 480

Ile Tyr Asp Asn Ala Phe Ile Ala Phe Val Asn Asp Leu Asp Pro Asn
                485                 490                 495

Lys Ala Gly Leu Leu Val Asn Trp Pro Thr Tyr Thr Ser Ser Ser Gln
            500                 505                 510

Ser Gly Asn Asn Met Met Met Ile Asn Ala Leu Gly Leu Tyr Thr Gly
        515                 520                 525

Lys Asp Asn Phe Arg Thr Ala Gly Tyr Asp Ala Leu Phe Ala Asn Pro
    530                 535                 540

Pro Ser Phe Phe Val
545

<210> SEQ ID NO 29
<211> LENGTH: 549
<212> TYPE: PRT
<213> ORGANISM: Candida cylindracea

<400> SEQUENCE: 29

Met Lys Leu Ala Leu Ala Leu Leu Ile Ala Ser Val Ala Ala Ala
1               5                   10                  15

Pro Thr Ala Lys Leu Ala Asn Gly Asp Thr Ile Thr Gly Leu Asn Ala
            20                  25                  30

Ile Ile Asn Glu Ala Phe Leu Gly Ile Pro Phe Ala Glu Pro Pro Val
        35                  40                  45

Gly Asn Leu Arg Phe Lys Asp Pro Val Pro Tyr Ser Gly Ser Leu Asn
    50                  55                  60

Gly Gln Lys Phe Thr Leu Tyr Gly Pro Leu Cys Met Gln Gln Asn Pro
65                  70                  75                  80

Glu Gly Thr Phe Glu Glu Asn Leu Gly Lys Thr Ala Leu Asp Leu Val
                85                  90                  95

Met Gln Ser Lys Val Phe Gln Ala Val Leu Pro Gln Ser Glu Asp Cys
            100                 105                 110

Leu Thr Ile Asn Val Val Arg Pro Pro Gly Thr Lys Ala Gly Ala Asn
        115                 120                 125

Leu Pro Val Met Leu Trp Ile Phe Gly Gly Gly Phe Glu Ile Gly Ser
    130                 135                 140

Pro Thr Ile Phe Pro Pro Ala Gln Met Val Thr Lys Ser Val Leu Met
```

```
                145                 150                 155                 160
Gly Lys Pro Ile Ile His Val Ala Val Asn Tyr Arg Val Ala Ser Trp
                    165                 170                 175
Gly Phe Leu Ala Gly Asp Asp Ile Lys Ala Glu Gly Ser Gly Asn Ala
                180                 185                 190
Gly Leu Lys Asp Gln Arg Leu Gly Met Gln Trp Val Ala Asp Asn Ile
            195                 200                 205
Ala Gly Phe Gly Gly Asp Pro Ser Lys Val Thr Ile Phe Gly Glu Leu
        210                 215                 220
Ala Gly Ser Met Ser Val Leu Cys His Leu Ile Trp Asn Asp Gly Asp
225                 230                 235                 240
Asn Thr Tyr Lys Gly Lys Pro Leu Phe Arg Ala Gly Ile Met Gln Leu
                245                 250                 255
Gly Ala Met Val Pro Leu Asp Pro Val Asp Gly Thr Tyr Gly Asn Glu
                260                 265                 270
Ile Tyr Asp Leu Phe Val Ser Ser Ala Gly Cys Gly Ser Ala Ser Asp
            275                 280                 285
Lys Leu Ala Cys Leu Arg Ser Ala Leu Ser Asp Thr Leu Leu Asp Ala
        290                 295                 300
Thr Asn Asn Thr Pro Gly Phe Leu Ala Tyr Ser Ser Leu Arg Leu Leu
305                 310                 315                 320
Tyr Leu Pro Arg Pro Asp Gly Lys Asn Ile Thr Asp Asp Met Tyr Lys
                325                 330                 335
Leu Val Arg Asp Gly Lys Tyr Ala Ser Val Pro Val Ile Ile Gly Asp
                340                 345                 350
Gln Asn Asp Glu Gly Thr Ile Phe Gly Leu Leu Leu Asn Val Thr
            355                 360                 365
Thr Asn Ala Gln Ala Arg Ala Tyr Phe Lys Gln Leu Phe Ile His Ala
        370                 375                 380
Ser Asp Ala Glu Ile Asp Thr Leu Met Ala Ala Tyr Pro Gln Asp Ile
385                 390                 395                 400
Thr Gln Gly Leu Pro Phe Asp Thr Gly Ile Phe Asn Ala Ile Thr Pro
                405                 410                 415
Gln Phe Lys Arg Ile Leu Ala Val Leu Gly Asp Leu Ala Phe Ile His
                420                 425                 430
Ala Arg Arg Tyr Phe Leu Asn His Phe Gln Gly Gly Thr Lys Tyr Ser
            435                 440                 445
Phe Leu Leu Lys Gln Leu Leu Gly Leu Pro Ile Met Gly Thr Phe His
        450                 455                 460
Ala Asn Asp Ile Val Trp Gln Asp Tyr Leu Leu Gly Ser Gly Ser Val
465                 470                 475                 480
Ile Tyr Asn Asn Ala Phe Ile Ala Phe Ala Thr Asp Leu Asp Pro Asn
                485                 490                 495
Thr Ala Gly Leu Leu Val Asn Trp Pro Lys Tyr Thr Ser Ser Leu Gln
                500                 505                 510
Leu Gly Asn Asn Leu Met Met Ile Asn Ala Leu Gly Leu Tyr Thr Gly
            515                 520                 525
Lys Asp Asn Phe Arg Thr Ala Gly Tyr Asp Ala Leu Met Thr Asn Pro
        530                 535                 540
Leu Leu Phe Phe Val
545

<210> SEQ ID NO 30
```

<211> LENGTH: 534
<212> TYPE: PRT
<213> ORGANISM: Candida sp. AC-IITM

<400> SEQUENCE: 30

```
Ala Pro Thr Ala Thr Leu Ala Asn Gly Asp Thr Ile Thr Gly Val Asn
1               5                   10                  15

Lys Ile Val Asn Glu Ala Phe Leu Gly Ile Pro Phe Ala Glu Pro Pro
            20                  25                  30

Val Gly Asn Leu Arg Phe Lys Asp Pro Val Pro Tyr Ser Arg Ser Leu
        35                  40                  45

Asn Gly Gln Lys Phe Thr Leu Asn Gly Pro Leu Cys Met Gln Met Asn
    50                  55                  60

Pro Leu Gly Asn Trp Asp Ser Ser Leu Pro Lys Ala Ala Ile Asn Leu
65                  70                  75                  80

Leu Met Gln Ser Lys Leu Phe Gln Ala Val Leu Pro Asn Gly Glu Asp
                85                  90                  95

Cys Leu Thr Ile Asn Val Val Arg Pro Leu Gly Thr Lys Pro Gly Ala
            100                 105                 110

Asn Leu Pro Val Met Val Trp Ile Phe Gly Gly Gly Phe Glu Val Gly
        115                 120                 125

Gly Ser Ser Leu Phe Pro Pro Ala Gln Met Ile Thr Ala Ser Val Leu
    130                 135                 140

Met Gly Lys Pro Ile Ile His Val Ser Met Asn Tyr Arg Val Ala Ser
145                 150                 155                 160

Trp Gly Phe Leu Ala Gly Pro Asp Ile Lys Ala Glu Gly Ser Gly Asn
                165                 170                 175

Ala Gly Leu His Asp Gln Arg Leu Gly Leu Gln Trp Val Ala Asp Asn
            180                 185                 190

Ile Ala Gly Phe Gly Gly Asp Pro Ser Lys Val Thr Ile Phe Gly Glu
        195                 200                 205

Leu Ala Gly Ser Met Ser Val Met Cys Gln Leu Leu Trp Asn Asp Gly
    210                 215                 220

Asp Asn Thr Tyr Asn Gly Lys Pro Leu Phe Arg Ala Ala Ile Met Gln
225                 230                 235                 240

Leu Gly Ala Met Val Pro Leu Asp Pro Val Asp Gly Pro Tyr Gly Thr
                245                 250                 255

Gln Ile Tyr Asp Gln Val Val Ala Ser Ala Gly Cys Gly Ser Ala Ser
            260                 265                 270

Asp Lys Leu Ala Cys Leu Arg Ser Ile Leu Asn Asp Lys Leu Phe Gln
        275                 280                 285

Ala Thr Ser Asp Thr Pro Gly Ala Leu Ala Tyr Pro Ser Leu Arg Leu
    290                 295                 300

Leu Phe Leu Pro Arg Pro Asp Gly Thr Phe Ile Thr Asp Asp Met Phe
305                 310                 315                 320

Lys Leu Val Arg Asp Gly Lys Cys Ala Asn Ile Pro Val Ile Ile Gly
                325                 330                 335

Asp Gln Asn Asp Glu Gly Thr Phe Phe Gly Thr Leu Leu Asn Val
            340                 345                 350

Thr Thr Asp Ala Gln Ala Arg Glu Tyr Phe Lys Gln Leu Phe Val His
        355                 360                 365

Ala Ser Asp Ala Glu Ile Asp Thr Leu Met Thr Ala Tyr Pro Gly Asp
    370                 375                 380

Ile Thr Gln Gly Leu Pro Phe Asp Thr Gly Ile Leu Asn Ala Leu Thr
```

-continued

```
385                 390                 395                 400
Pro Gln Phe Lys Arg Ile Leu Ala Val Leu Gly Asp Leu Gly Phe Thr
                405                 410                 415

Leu Ala Arg Arg Tyr Phe Leu Asn His Tyr Thr Gly Gly Thr Lys Tyr
                420                 425                 430

Ser Phe Leu Leu Lys Gln Leu Leu Gly Leu Pro Val Leu Gly Thr Phe
            435                 440                 445

His Ser Asn Asp Ile Val Phe Gln Asp Tyr Leu Leu Gly Ser Gly Ser
        450                 455                 460

Leu Ile Tyr Asn Asn Ala Phe Ile Ala Phe Ala Thr Asp Leu Asp Pro
465                 470                 475                 480

Asn Thr Ala Gly Leu Leu Val Lys Trp Pro Glu Tyr Thr Ser Ser Leu
                485                 490                 495

Gln Leu Gly Asn Asn Leu Met Met Ile Asn Ala Leu Gly Leu Tyr Thr
                500                 505                 510

Gly Lys Asp Asn Phe Arg Thr Ala Gly Tyr Asp Ala Leu Phe Ser Asn
            515                 520                 525

Pro Leu Leu Phe Phe Val
        530
```

MODIFIED LIPASE AND USE THEREOF

TECHNICAL FIELD

The present invention relates to a modified lipase. In particular, the present invention provides a modified lipase with improved reactivity and/or stability at a high temperature, and use thereof. This application claims priority to Japanese Patent Application No. 2017-168995, filed on Sep. 1, 2017, the entire contents of which are hereby incorporated by reference.

BACKGROUND ART

A lipase is an enzyme that acts on ester bonds in lipids. Lipases of various origins have been isolated, and are used, for example, for the degradation of fats and oils, food processing, and production of pharmaceuticals. For example, a *Candida cylindracea*-derived lipase (previously referred to as a *Candida rugosa*-derived lipase) is expected to be used in fields such as wastewater treatment and food processing (see, for example, PTLs 1 to 3 and NPL 1).

CITATION LIST

Patent Literature

[PTL 1] WO 2012/077614
[PTL 2] JP-A 2017-73980
[PTL 3] JP-A 2003-144162

Non Patent Literature

[NPL 1] Shuji, AKAI, Development of Novel Asymmetric Reactions Oriented to Next-Generation Enzymatic Organic Syntheses, *YAKUGAKU ZASSHI*, Vol. 123 (2003) No. 11, pages 919-931

SUMMARY OF INVENTION

Technical Problem

A *Candida cylindracea*-derived lipase has high industrial utility. However, there is room for improvement in the stability and reactivity of the lipase at a high temperature. If improvements in its stability/reactivity at a high temperature are made, then it will be possible that it provides increased productivity and expanded use. Therefore, the present invention aims at making improvements in the stability/reactivity of the *Candida cylindracea*-derived lipase at a high temperature, thereby increasing its usefulness or utility value.

Solution to Problem

In order to address the above subject, the present inventors undertook to modify a *Candida cylindracea*-derived lipase. After trial and error, the present inventors were successful in identifying mutation points (amino acid residues) effective for the improvement in the reactivity or stability of the lipase at a high temperature, whereby highly useful variants (modified lipases) were obtained. This result is also important in providing information and means for designing and obtaining variants of a given enzyme that can achieve the purpose of improving the reactivity and stability thereof at a high temperature.

On the other hand, many cases are also encountered in which it is highly likely that for a given enzyme, combinations of two effective mutations result in additive or synergistic effects. In addition, in light of the common technical knowledge that enzymes of the same kind show high levels of similarity in their structures (primary structures and steric structures) and it is highly probable that for these enzymes, a similar mutation leads to similar effects, if a mutations that has been found to be useful in a *Candida cylindracea*-derived lipase having the amino acid sequence represented by SEQ ID NO: 1 is applied to another lipase having a high structural similarity relative to the *Candida cylindracea*-derived lipase, then there is a high probability that such a lipase has effects comparable to those achieved in the *Candida cylindracea*-derived lipase. Moreover, one skilled in the art could recognize that this approach is effective.

The present invention described below are based on the above-mentioned results and considerations.

[1] A modified lipase with improved reactivity and/or stability at a high temperature, as compared to a lipase consisting of an amino acid sequence represented by SEQ ID NO: 1, the modified lipase having an amino acid sequence comprising one or more amino acid substitutions which are selected from the group consisting of T130C-S153C, A249P, F259Y, S282P, S283Y, and S300P in the amino acid sequence represented by SEQ ID NO: 1, or an amino acid sequence having 90% or more sequence identity therewith.

[2] The modified lipase according to [1], wherein the amino acid substitution contained in the amino acid sequence of the modified lipase is T130C-S153C or S283Y, and the modified lipase has improved reactivity at a high temperature.

[3] The modified lipase according to [1], wherein the amino acid substitution contained in the amino acid sequence of the modified lipase is A249P, S283Y, or S300P, and the modified lipase has improved stability at a high temperature.

[4] A lipase with improved reactivity and/or stability at a high temperature, as compared to a lipase consisting of an amino acid sequence represented by SEQ ID NO: 1, comprising the amino acid sequence represented by any of SEQ ID NOs: 2 to 7, or an amino acid sequence having 90% or more sequence identity therewith, with the proviso that the amino acid sequence is different at a position or positions other than those corresponding to cysteine at positions 130 and 153 in the amino acid sequence represented by SEQ ID NO: 2, proline at position 249 in the amino acid sequence represented by SEQ ID NO: 3, tyrosine at position 259 in the amino acid sequence represented by SEQ ID NO: 4, proline at position 282 in the amino acid sequence represented by SEQ ID NO: 5, tyrosine at position 283 in the amino acid sequence represented by SEQ ID NO: 6, and proline at position 300 in the amino acid sequence represented by SEQ ID NO: 7, when the respective amino acid sequences are used as a reference sequence to determine the sequence identity.

[5] A gene encoding the modified lipase according to any one of [1] to [4].

[6] The gene according to [5], comprising a base sequence represented by any of SEQ ID NOs: 8 to 19.

[7] A recombinant DNA containing the gene according to [5] or [6].

[8] A microorganism carrying the recombinant DNA according to [7].

[9] The microorganism according to [8], wherein the host is *Escherichia coli*, *Candida cylindracea*, *Aspergillus oryzae*, *Bacillus subtilis*, or *Pichia pastoris*.

[10] An enzyme preparation comprising the modified lipase according to any one of [1] to [4].

[11] A method for degradation of fats and oils, characterized in that the enzyme according to any one of [1] to [4] or the enzyme preparation according to [10] is allowed to act on the fats and oils to carry out an enzyme reaction.

[12] The method for degradation according to [11], wherein the enzyme reaction is carried out at 30° C. to 70° C.

[13] A method for preparing a modified lipase, comprising the steps of:
(I) providing a nucleic acid encoding an amino acid sequence represented by any of SEQ ID NOs: 2 to 7;
(II) expressing the nucleic acid; and
(III) recovering the expression product.

DESCRIPTION OF EMBODIMENTS

Figure 1:
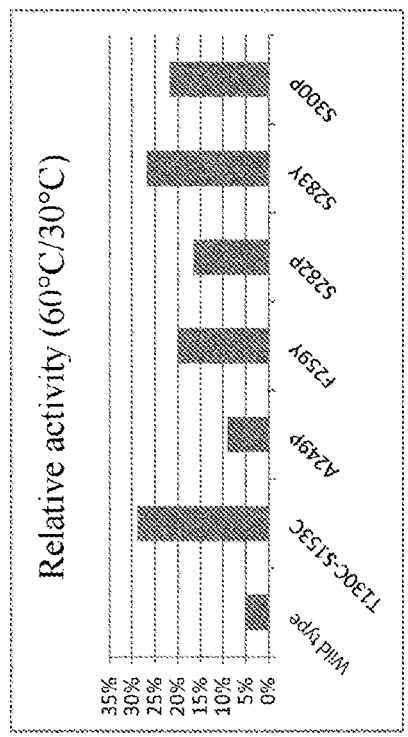
FIG. 1 The reactivity of variants at a specified high temperature. Relative activities of the variants (ratios of enzyme activity at 60° C. to that at 30° C.) were compared with that of the wild-type enzyme.

For convenience of description, some of the terms used in relation to the present invention are defined as follows.

Terminology

The term "modified lipase" refers to an enzyme obtained by modification or mutation of a particular lipase (which is referred to as a "reference lipase" for convenience of description). Typically, the reference lipase is a *Candida cylindracea* derived lipase having the amino acid sequence of SEQ ID NO:1. The terms "*Candida cylindracea* derived lipase" and "*Candida rugosa* derived lipase" are used interchangeably.

The term "*Candida cylindracea* derived lipase" is a lipase that is obtained from a strain of *Candida cylindracea* as the source, and includes lipases produced by *Candida cylindracea*, lipases expressed, for example, in other microorganism, using the genetic information of such enzyme, or the like.

In the present invention, an "amino acid substitution" is carried out as modification or mutation. Therefore, some amino acid residues are found to be different when a modified lipase and the reference lipase therefor are compared. In the specification, a modified lipase is also referred to as a modified enzyme or as a variant.

In the specification, amino acids are designated according to the common practice, as their single letters as described below:
methionine: M; serine: S; alanine: A; threonine: T; valine: V; tyrosine: Y; leucine: L; asparagine: N; isoleucine: I; glutamine: Q; proline: P; aspartic acid: D; phenylalanine: F; glutamic acid: E; tryptophan: W; lysine: K; cysteine: C; arginine: R; glycine: G; and histidine: H.

In the specification, the positions of amino acids in an amino acid sequence are specified by assigning the numbers from the N-terminus toward the C-terminus of the amino acid sequence, wherein the amino acid residue at the N-terminus of a mature protein in which the signal peptide has been removed is assigned to 1, i.e., the first amino acid.

In the specification, an amino acid residue at a mutation site (an amino acid residue to be substituted with another amino acid) is expressed in a combination of the above-described single letter representing the kind of the amino acid residue and the figure representing the position of the amino acid residue. For example, a mutation which substitutes threonine at position 130 for cysteine is designated as "T130C".

1. Modified Lipases

A first aspect of the present invention relates to a modified lipase (or a modified enzyme). A modified enzyme according to the present invention typically has an amino acid sequence comprising one or more amino acid substitutions selected from the group consisting of T130C-S153C, A249P, F259Y, S282Y, S283Y, and S300P in the amino acid sequence represented by SEQ ID NO: 1. Due to this feature, the modified lipase has improved reactivity or stability, or improved reactivity and stability, at a high temperature, as compared to a lipase consisting of the amino acid sequence represented by SEQ ID NO: 1. The amino acid sequence represented by SEQ ID NO: 1 corresponds to the mature form (that is, without signal peptide) of *Candida cylindracea*-derived lipase (referred to herein as "LIP1").

In order to facilitate understanding and judgment/determination of the high-temperature reactivity and stability of modified enzymes, the high temperature at which they are measured for their high-temperature reactivity is set to be "55° C. to 65° C." and the high temperature at which they are measured for their high-temperature stability is set to be "45° C. to 55° C."

The high-temperature reactivity of modified enzymes can be evaluated based on, for example, the ratio of enzyme activity at 60° C. to that at 30° C. (relative activity at 60° C. with respect to that at 30° C.). A modified enzyme according to the present invention has improved high-temperature reactivity as compared to a reference lipase, that is, a lipase consisting of the amino acid sequence represented by SEQ ID NO: 1, and thus the relative activity of the modified enzyme will be higher than that of the reference lipase. The relative activity of the modified enzymes is, for example, 1.5 to 10 times that of the reference lipase. Preferably, the relative activity of the modified enzymes is 3 to 10 times that of the reference lipase. Here, the relative activity is calculated as follows.

Relative activity=(enzyme activity at 60° C./enzyme activity at 30° C.)×100(%)

The high-temperature stability of modified enzymes can be evaluated based on, for example, the residual activity after treatment at 50° C. for 30 minutes. A modified enzyme according to the present invention has improved high-temperature stability as compared to a reference lipase, that is, a lipase consisting of the amino acid sequence represented by SEQ ID NO: 1, and thus the residual activity percent of the modified enzyme will be higher than that of the reference lipase. The residual activity percent of the modified enzymes is, for example, 1.1 to 2.0 times that of the reference lipase. Preferably, the residual activity percent of the modified enzymes is 1.5 to 2.0 times that of the reference lipase. Here, the residual activity percent is calculated as follows.

Residual activity percent=(enzyme activity after heat treatment/enzyme activity before heat treatment)×100(%)

As used herein, "comprising an amino acid substitution" means that the substituted amino acid is located at the mutation point, that is, the position of the amino acid residue at which a specified amino acid substitution occurs. Therefore, when an amino acid sequence comprising an amino acid substitution, i.e., a mutated amino-acid sequence, is compared with that represented by SEQ ID NO: 1 (reference amino-acid sequence) having no amino acid substitution, the mutated amino-acid sequence will be found to have a different amino acid residue at the position at which the amino acid substitution has occurred.

T130C-S153C denotes a mutation in which the amino acid at position 130 (threonine) in the amino acid sequence represented by SEQ ID NO: 1 is substituted with cysteine and the amino acid at position 153 (serine) is substituted with cysteine. A249P denotes a mutation in which the amino acid at position 249 (alanine) in the amino acid sequence represented by SEQ ID NO: 1 is substituted with proline. F259Y denotes a mutation in which the amino acid at position 259 (phenylalanine) in the amino acid sequence represented by SEQ ID NO: 1 is substituted with tyrosine. S282P denotes a mutation in which the amino acid at position 282 (serine) in the amino acid sequence represented by SEQ ID NO: 1 is substituted with proline. S283Y denotes a mutation in which the amino acid at position 283 (serine) in the amino acid sequence represented by SEQ ID NO: 1 is substituted with tyrosine. S300P denotes a mutation in which the amino acid at position 300 (serine) in the amino acid sequence represented by SEQ ID NO: 1 is substituted with proline.

Specific examples of a modified enzyme according to the present invention can include lipases consisting of the amino acid sequence represented by any of SEQ ID NOs: 2 to 7, corresponding to variants 1 (T130C-S153C), 2 (A249P), 3 (F259Y), 4 (S282P), 5 (S283Y), and 6 (S300P) in this order. As shown in Examples described below, a lipase consisting of the amino acid sequence represented by SEQ ID NO: 2 (variant 1 (T130C-S153C)) and a lipase consisting of the amino acid sequence represented by SEQ ID NO: 6 (variant 5 (S283Y)) have been ascertained to show particularly improved reactivity at the high temperature. On the other hand, a lipase consisting of the amino acid sequence represented by SEQ ID NO: 3 (variant 2 (A249P)), a lipase consisting of the amino acid sequence represented by SEQ ID NO: 6 (variant 5 (S283Y)), and a lipase consisting of the amino acid sequence represented by SEQ ID NO: 7 (variant 6 (S300P)) have been ascertained to show particularly improved stability at the high temperature.

Generally, when the amino acid sequence of a given protein is partially changed by mutation, the protein obtained after the mutation may have the same function as that before the mutation. In other words, it is sometimes observed that a mutation in the amino acid sequence of a given protein does not substantially affect the function of the resulting protein and in these proteins, the function is maintained before and after the mutation. In addition, it is highly probable that two proteins exhibit equivalent properties when sharing high identity in their amino acid sequences. In light of common technical knowledge of these things, a modified enzyme can be considered to be an enzyme that is substantially identical to the above-described modified enzyme (or can be referred to as a substantially identical lipase), with the proviso that such a modified enzyme has an amino acid sequence that is not completely identical (i.e., does not have a sequence identity of 100%) to that of any of the above-described modified enzymes, that is, an "amino acid sequence comprising one or more amino acid substitutions selected from the group consisting of T130C-S153C, A249P, F259Y, S282P, S283Y, and S300P in the amino acid sequence represented by SEQ ID NO: 1 (specific examples of which amino acid sequence are those represented by SEQ ID NOs: 2 to 7)" and displays a high level of sequence identity therewith, and has improved reactivity and/or stability at a high temperature. Such a high level of sequence identity is preferably 90% or more, more preferably 95% or more, even more preferably 98% or more, and most preferably 99% or more. If a substantially identical lipase is compared with the above-described modified enzyme, then the lipase will be found to have a slightly different amino acid sequence. Note that a slight difference in the amino acid sequence of a substantially identical lipase is to be generated at a position or positions other than that at which the above-mentioned amino acid substitution is made. Accordingly, a slight difference in the amino acid sequence of a substantially identical lipase will be generated at a position or positions other than those corresponding to cysteine at positions 130 and 153 in the amino acid sequence represented by SEQ ID NO: 2, proline at position 249 in the amino acid sequence represented by SEQ ID NO: 3, tyrosine at position 259 in the amino acid sequence represented by SEQ ID NO: 4, proline at position 282 in the amino acid sequence represented by SEQ ID NO: 5, tyrosine at position 283 in the amino acid sequence represented by SEQ ID NO: 6, and proline at position 300 in the amino acid sequence represented by SEQ ID NO: 7, when the respective amino acid sequences are used as a reference sequence to determine the sequence identity. In other words, in amino acid sequences having a sequence identity of 90% or more with that represented by SEQ ID NO: 2, both the amino acids at the positions corresponding to positions 130 and 153 therein are cysteine. Similarly, in amino acid sequences having a sequence identity of 90% or more with that represented by SEQ ID NO: 3, the amino acid at the position corresponding to position 249 therein is proline; in amino acid sequences having a sequence identity of 90% or more with that represented by SEQ ID NO: 4, the amino acid at the position corresponding to position 259 therein is tyrosine; in amino acid sequences having a sequence identity of 90% or more with that represented by SEQ ID NO: 5, the amino acid at the position corresponding to position 282 therein is proline; in amino acid sequences having a sequence identity of 90% or more with that represented by SEQ ID NO: 6, the amino acid at the position corresponding to position 283 therein is tyrosine; and in amino acid sequences having a sequence identity of 90% or more with that represented by SEQ ID NO: 7, the amino acid at the position corresponding to position 300 therein is proline.

Here, a "slightly different amino acid sequence" results from amino acid deletion, substitution, addition, insertion, or a combination thereof. This means that in typical cases, a given amino acid sequence is mutated (or changed) by deletion or substitution of one to several (for example, up to three, five, seven, ten) amino acids constituting the amino acid sequence, or addition or insertion of one to several (for example, up to three, five, seven, ten) amino acids, or a combination thereof. A "slightly different amino acid sequence" preferably results from a conservative amino acid substitution. Here, by "conservative amino acid substitution" is meant that a certain amino acid residue is substituted with an amino acid residue of which the side chain is similar in properties. Amino acid residues are classified into several families, on the basis of their side chains, such as families of amino acids having basic side chains (for example, lysine, arginine, histidine), acidic side chains (for example, aspartic acid, glutamic acid), uncharged polar side chains (e.g. glycine, asparagine, glutamine, serine, threonine, tyrosine, cysteine), nonpolar side chains (for example, alanine, valine, leucine, isoleucine, proline, phenylalanine, methionine, tryptophan), β-branched side chains (for example, threonine, valine, isoleucine), and aromatic side chains (for example, tyrosine, phenylalanine, tryptophan, histidine). The conservative amino acid substitution preferably is a substitution between amino acid residues within the same family. In connection with this, it is known that the amino acid residues constituting the active center of *Candida cylindracea*-derived lipase (LIP1) (SEQ ID NO: 1) are glutamic acid at position 341, histidine at position 449, and serine at position 209, and thus mutation should be made so that there is no influence on these amino acid residues. An example of an amino acid sequence in which a slightly different amino acid sequence does not substantially affect the function of the resulting protein and the function is maintained before and after the mutation is one in which the amino acid at position 206 in the amino acid sequence represented by SEQ ID NO: 1 (phenylalanine) is changed to tyrosine. A lipase having this mutated amino acid sequence was found equivalent to a lipase having the amino acid sequence represented by SEQ ID NO: 1 when specific activities and high-temperature reactivities were compared.

The identity (%) between two amino acid sequences or two nucleic acid sequences (hereinafter, the term "two sequences" are used for representing either of two sequences) can be determined by the following procedure. Firstly, two sequences are aligned for optimum comparison of the two sequences (for example, a gap may be introduced into the first sequence so as to optimize the alignment with respect to the second sequence). When a molecule (amino acid residue or nucleotide) at a specific position in the first sequence and a molecule in the corresponding position in the second sequence are the same as each other, the molecules in the positions are defined as being identical. The identity between two sequences is a function of the number of identical positions shared by the two sequences (i.e., identity (%)=number of identical positions/total number of positions×100). Preferably, the number and size of the gaps, which are required to optimize the alignment of the two sequences, are taken into consideration.

The comparison and determination of the identity between two sequences can be carried out by using a mathematical algorithm. A specific example of the mathematical algorithm that can be used for comparing the sequences includes an algorithm described in Karlin and Altschul (1990) Proc. Natl. Acad. Sci. USA 87:2264-68 and modified by Karlin and Altschul (1993) Proc. Natl. Acad. Sci. USA 90:5873-77. However, the algorithm is not necessarily limited to this. Such an algorithm is incorporated in NBLAST program and XBLAST program (version 2.0) described in Altschul et al. (1990) J. Mol. Biol. 215: 403-10. In order to obtain an equivalent nucleic acid sequence, for example, BLAST nucleotide search with score=100 and word length=12 may be carried out by the NBLAST program. In order to obtain an equivalent amino acid sequence, for example, BLAST polypeptide search with score=50 and word length=3 may be carried out by the XBLAST program. In order to obtain gapped alignments for comparison, Gapped BLAST described in Altschul et al., (1997) Amino Acids Research 25(17): 3389-3402 can be utilized. In using BLAST and Gapped BLAST, the default parameters of the corresponding programs (e.g., XBLAST and NBLAST) can be used. In detail, see http://www.ncbi.nlm.nih.gov. Another example of the mathematical algorithm that can be used for comparing sequences includes an algorithm described in Meyers and Miller (1988) Comput. Appl. Biosci. 4: 11-17. Such programs are incorporated into the ALIGN program that can be used for, for example, GENESTREAM network server (IGH Montpellier, France) or ISREC server. When the ALIGN program is used for comparison of the amino acid sequences, for example, PAM120 weight residue table can be used in which a gap length penalty is 12 and a gap penalty is 4.

The identity between two amino acid sequences can be determined by using the GAP program in the GCG software package, using Blossom 62 matrix or PAM250 matrix with the gap weight of 12, 10, 8, 6, or 4, and the gap length weight of 2, 3, or 4. The identity between two nucleic acid sequences can be determined by using the GAP program in the GCG software package (available at http://www.gcg.com), with the gap weight of 50, and the gap length weight of 3.

Typically, a modified enzyme according to the present invention is produced by subjecting a lipase consisting of the amino acid sequence represented by SEQ ID NO: 1, that is, *Candida cylindracea*-derived lipase, to mutation (one or a combination of two or more of the above-described T130C-S153C, A249P, F259Y, S282P, S283Y, and S300P). A substantially identical lipase as mentioned above can be obtained by subjecting a lipase consisting of the amino acid sequence represented by SEQ ID NO: 1 to mutation (one or a combination of two or more of the above-described T130C-S153C, A249P, F259Y, S282P, S283Y, and S300P), followed by further mutation, or by applying an equivalent mutation to a lipase consisting of an amino acid sequence having a high sequence identity with that represented by SEQ ID NO: 1, such as a lipase derived from a strain of the same genera and species as a strain of *Candida cylindracea* that produces a lipase consisting of the amino acid sequence represented by SEQ ID NO: 1, or subjecting a variant resulting therefrom to additional mutation. The "equivalent mutation" in this case will lead to a substitution being made at an amino acid residue corresponding to that at any of the mutation points disclosed in the present invention (position 130, 153, 249, 259, 282, 283, or 300 in the amino acid sequence represented by SEQ ID NO: 1), in an amino acid sequence having a high sequence identity with that represented by SEQ ID NO: 1. Examples of a lipase consisting of an amino acid sequence having a high sequence identity with that represented by SEQ ID NO: 1 can be, by way of illustration, isozymes of LIP1, i.e., LIP2 (SEQ ID NO: 24, showing a sequence identity of 79%), LIP3 (SEQ ID NO: 25, showing a sequence identity of 88%), LIP4 (SEQ ID NO: 26, showing a sequence identity of 81%), and LIP5 (SEQ ID NO: 27, showing a sequence identity of 82%), and lipases derived from *Diutina rugosa* (SEQ ID NO: 28, showing a sequence identity of 87%), *Candida cylindracea* (SEQ ID NO: 29, showing a sequence identity of 85%), and *Candida* sp. AC-IITM (SEQ ID NO: 30, showing a sequence identity of 84%).

Herein, the term "corresponding" when used for an amino acid residue in the present specification means contributing equally to exhibition of functions among proteins (enzymes) being compared. For example, when an amino acid sequence for comparison to the base amino acid sequence (that is, the amino acid sequence set forth in SEQ ID NO: 1) is aligned while considering partial homology of the primary structure (that is, an amino acid sequence) so that the most appropriate comparison can be achieved (in this event, the alignment may be optimized by introducing gaps if necessary), an amino acid located at a position corresponding to a specific amino acid in the base amino acid sequence can be specified as a "corresponding amino acid". The "corresponding amino acid" can also be specified by comparison between conformations (three-dimensional structures) in place of or in addition to the comparison between primary structures. Utilization of conformational information can give highly credible comparison results. In this case, a technique of performing an alignment with comparing atomic coordinates of conformations of a plurality of enzymes can be adopted. Conformational information of an enzyme to be mutated is available from, for example, the Protein Data Bank (http://www.pdbj.org/index_j.html).

One example of a method for determination of a protein conformation by the X-ray crystal structure analysis will be shown below.

(1) A protein is crystallized. Crystallization is essential to determine a conformation, and in addition, crystallization is industrially useful as a purification method of a protein at high purity and a stable preservation method of a protein at high density. In this case, a protein to which a substrate as a ligand or its analogous compound is bound may be preferably used for crystallization.

(2) The prepared crystal is irradiated with X ray to collect diffraction data. There are many cases that a protein crystal is damaged due to X ray irradiation and the diffraction ability is deteriorated. In such cases, a low-temperature measurement technique of rapidly cooling the crystal to about −173° C. and collecting diffraction data in the state has been recently prevailed. In addition, ultimately, synchrotron orbit radiation having high luminance is utilized to collect high resolution data that is used for structural determination.

(3) In addition to the diffraction data, phase information is necessary in order to perform the crystal structure analysis. When a crystal structure of an analogous protein to a desired protein is unknown, it is impossible to determine the structure in a molecular substitution method, and a phase problem has to be solved by a heavy-atom isomorphous replacement method. The heavy-atom isomorphous replacement method is a method in which a metallic atom having a high atomic number such as mercury or platinum is introduced into a crystal and contribution of a large X ray scattering ability of such a metallic atom to X ray diffraction data is utilized to collect phase information. The determined phase is possibly improved by smoothing an electron density of a solvent region in the crystal. Since a water molecule in the solvent region has large fluctuation, the electron density is hardly observed, and thus adjusting the electron density in this region to close to 0 makes it possible to approach the real electron density, which results in improving a phase. When plural molecules are contained in an asymmetrical unit, equation of electron densities of these molecules makes it possible to more significantly improve a phase. A model of a protein is fit to an electron density map calculated using the phase improved as described above. This process is performed on computer graphics using a program such as QUANTA made by MSI Co. (USA). After the process, structural precision is performed using a program such as X-PLOR made by MSI Co. to complete the structure analysis. When a crystal structure of an analogous protein to a desired protein is known, it can be determined in a molecular substitution method using the atomic coordinate of the known protein. Molecular substitution and structure refinement can be performed using a program such as CNS_SOLVE ver. 11.

2. Nucleic Acid Coding for Modified Lipase, etc.

The second aspect of the present invention provides a nucleic acid relating to the modified enzyme of the invention. That is, provided are a gene coding for the modified enzyme, a nucleic acid that can be used as a probe for identifying a nucleic acid coding for the modified enzyme, and a nucleic acid that can be used as a primer for amplifying or mutating a nucleic acid coding for the modified enzyme.

The gene coding for a modified enzyme is typically used in preparation of the modified enzyme. According to a genetic engineering procedure using the gene coding for a modified enzyme, a modified enzyme in a more homogeneous state can be obtained. Further, the method can be a preferable method also in the case of preparing a large amount of a modified enzyme. Note that uses of the gene coding for a modified enzyme are not limited to preparation of a modified enzyme. For example, the nucleic acid can also be used as a tool for an experiment intended for clarification of action mechanisms of a modified enzyme or a tool for designing or preparing a further modified form of an enzyme.

The "gene coding for a modified enzyme" herein refers to a nucleic acid capable of obtaining the modified enzyme when it is expressed, and includes, as a matter of course of a nucleic acid having a base sequence corresponding to the amino acid sequence of the modified enzyme, also a nucleic acid obtained by adding a sequence that does not code for an amino acid sequence to such a nucleic acid. Degeneracy of a codon is also considered.

Examples of the (base) sequence of the gene encoding a modified enzyme are represented in SEQ ID NOs: 8 to 13. These sequences encode variants described in the Examples section which follows, as indicated below.

SEQ ID NO: 8: variant 1 (T130C-S153C)
SEQ ID NO: 9: variant 2 (A249P)
SEQ ID NO: 10: variant 3 (F259Y)
SEQ ID NO: 11: variant 4 (S282P)
SEQ ID NO: 12: variant 5 (S283Y)
SEQ ID NO: 13: variant 6 (S300P)

In *Candida cylindracea*, the CTG codon encodes serine. If a gene is recombinantly expressed using other yeasts and the like as a host, then it is necessary that depending on the host to be used, the CTG codon is changed to another codon encoding serine (TCT, TCC, TCA, ATG, or AGC). The present invention also provides, as the sequence of a gene for use in heterologous expression, a sequence in which a codon substitution of this type is made for the sequence of any one of SEQ ID NOs: 8 to 13. Examples of sequences with a codon substitution are as follows.

SEQ ID NO: 14, which is a sequence with a codon substitution in the sequence of SEQ ID NO: 8;

SEQ ID NO: 15, which is a sequence with a codon substitution in the sequence of SEQ ID NO: 9;

SEQ ID NO: 16, which is a sequence with a codon substitution in the sequence of SEQ ID NO: 10;

SEQ ID NO: 17, which is a sequence with a codon substitution in the sequence of SEQ ID NO: 11.

SEQ ID NO: 18, which is a sequence with a codon substitution in the sequence of SEQ ID NO: 12. and SEQ ID NO: 19, which is a sequence with a codon substitution in the sequence of SEQ ID NO: 13.

When a gene according to the present invention is to be expressed in a host, the gene will usually be inserted into the host in the form of a gene construct in which the above-described sequence has a signal peptide-coding sequence (a signal sequence) added thereto at the 5' end of the above sequence (any one of SEQ ID NOs:8-19). The signal sequence of wild-type LIP1 is represented in SEQ ID NO: 20. The amino acid sequence encoded by this signal sequence (that is, the signal peptide) is represented in SEQ ID NO: 21. The signal sequence may be selected depending on the host to be used. Any signal sequence that can express a variant of interest can be used in the present invention.

Examples of the signal sequence that can be used in the present invention can be illustrated by the following: a sequence encoding the signal peptide of the α-factor (Protein Engineering, 1996, vol. 9, p. 1055-1061), a sequence encoding the signal peptide of the α-factor receptor, a sequence encoding the signal peptide of the SUC2 protein, a sequence encoding the signal peptide of the PHO5 protein, a sequence encoding the signal peptide of the BGL2 protein, a sequence encoding the signal peptide of the AGA2 protein, a sequence encoding the signal peptide of TorA (trimethylamine N-oxidoreductase), a sequence encoding the signal peptide of *Bacillus subtilis* derived PhoD (phosphoesterase), a sequence encoding the signal peptide of *Bacillus subtilis* derived LipA (lipase), a sequence encoding the signal peptide of *Aspergillus oryzae* derived Taka-amylase (JP 2009-60804 A), a sequence encoding the signal peptide of *Bacillus amyloliquefaciens* derived α-amylase (Eur. J. Biochem. 155, 577-581 (1986)), a sequence encoding the signal peptide of *Bacillus subtilis* derived neutral protease (APPLIED AND ENVIRONMENTAL MICROBIOLOGY, April 1995, p. 1610-1613, Vol. 61, No. 4), and a sequence encoding the signal peptide of *Bacillus* derived cellulase (JP 2007-130012 A).

The nucleic acid of the present invention can be prepared in an isolated state by use of a standard genetic engineering technique, molecular biological technique, biochemical technique, chemical synthesis and the like in reference to the present specification or the sequence information disclosed in the appended sequence listing.

Another embodiment of the present invention provides a nucleic acid different in a base sequence in a part (hereinafter also referred to as a "homologous nucleic acid", and a base sequence defining a homologous nucleic acid is also referred to as a "homologous base sequence") as compared to the base sequence of the gene coding for the modified enzyme of the invention, although functions of a protein coded by the nucleic acid are equal. An example of the homologous nucleic acid includes a DNA composed of a base sequence containing substitution, deletion, insertion, addition or inversion of 1 to several bases on the basis of the base sequence of the nucleic acid coding for the modified enzyme of the present invention and coding for a protein having activity which is characteristic to the modified enzyme (i.e. lipase activity). Substitution or deletion of bases may occur in a plurality of sites. The "plurality" herein depends on positions or kinds of amino acid residues in a conformation of a protein coded by the nucleic acid but means, for example, 2 to 40 bases, preferably 2 to 20 bases, and more preferably 2 to 10 bases.

The homologous nucleic acid has, for example, a sequence identity of 60% or more, preferably 70% or more, more preferably 80% or more, even more preferably 85% or more, further preferably about 90% or more, still further preferably 95% or more, most preferably 99% or more, with a reference base sequence.

Such a homologous nucleic acid as described above can be obtained by, for example, a restriction enzyme treatment, a treatment with exonuclease, DNA ligase, etc., and introduction of mutation by a site directed mutation introduction method (Molecular Cloning, Third Edition, Chapter 13, Cold Spring Harbor Laboratory Press, New York), and random mutation introduction method (Molecular Cloning, Third Edition, Chapter 13, Cold Spring Harbor Laboratory Press, New York). The homologous nucleic acid can be obtained also in other methods such as exposure to ultraviolet radiation.

Another embodiment of the present invention relates to a nucleic acid having a base sequence complementary to the base sequence of the gene coding for the modified enzyme of the invention. Another embodiment of the present invention provides a nucleic acid having a base sequence with an identity of at least about 60%, 70%, 80%, 90%, 95%, 99%, or 99.9% to the base sequence of the gene coding for the modified enzyme of the invention or a base sequence complementary to the base sequence.

Another embodiment of the present invention relates to a nucleic acid having a base sequence hybridizing to a base sequence complementary to the base sequence of the gene coding for the modified enzyme of the invention or its homologous base sequence under stringent conditions. The "stringent conditions" herein refer to conditions wherein a so-called specific hybrid is formed and a nonspecific hybrid is not formed. Such stringent conditions are known by a person skilled in the art and can be set in reference to, for example, Molecular Cloning (Third Edition, Cold Spring Harbor Laboratory Press, New York) and Current protocols in molecular biology (edited by Frederick M. Ausubel et al., 1987). Examples of the stringent conditions include conditions of using a hybridization liquid (50% formamide, 10×SSC (0.15 M NaCl, 15 mM sodium citrate, pH 7.0), a 5×Denhardt solution, 1% SDS, 10% dextran sulfate, 10 μg/ml of modified salmon sperm DNA, and a 50 mM phosphate buffer (pH 7.5)) and incubating at about 42° C. to about 50° C., thereafter washing with 0.1×SSC and 0.1% SDS at about 65° C. to about 70° C. Examples of more preferable stringent conditions include conditions of using 50% formamide, 5×SSC (0.15 M NaCl, 15 mM sodium citrate, pH 7.0), a 1×Denhardt solution, 1% SDS, 10% dextran sulfate, 10 μg/ml of modified salmon sperm DNA, and a 50 mM phosphate buffer (pH 7.5) as a hybridization liquid.

Another embodiment of the present invention provides a nucleic acid (nucleic acid fragment) having a part of the base sequence of the gene coding for the modified enzyme of the invention or a base sequence complementary to the base sequence. Such a nucleic acid fragment can be used in detection, identification, and/or amplification of a nucleic acid having the base sequence of the gene coding for the modified enzyme of the present invention. For example, the nucleic acid fragment is designed so as to at least contain a part being hybridized to a sequential nucleotide moiety (for example, about 10 to about 100 bases length, preferably about 20 to about 100 bases length, more preferably about 30 to about 100 bases length) in the base sequence of the gene coding for the modified enzyme of the invention. When used as a probe, the nucleic acid fragment can be labeled. Examples such as fluorescent substances, enzymes, and radioactive isotopes can be used for the labeling.

Another aspect of the present invention relates to a recombinant DNA containing the gene of the present invention (the gene coding for a modified enzyme). The recombinant DNA of the invention is provided in, for example, a form of a vector. The term "vector" in the present specification refers to a nucleic acid molecule that can transfer a nucleic acid inserted in the vector to a target such as a cell.

A suitable vector is selected according to its intended use (cloning, expression of a protein) and in consideration of a kind of a host cell. Examples include a M13 phage or an altered form thereof, a λ phage or an altered form thereof, and pBR322 or an altered form thereof (e.g., pB325, pAT153, pUC8), etc. as a vector having *Escherichia coli* as a host, pYepSec1, pMFa, pYES2 and pPIC3.5K as a vector having a yeast as a host, pAc, pVL, etc. as a vector having an insect cell as a host, and pCDM8, pMT2PC, etc. as a vector having a mammal cell as a host.

The vector of the present invention is preferably an expression vector. The "expression vector" refers to a vector capable of introducing a nucleic acid inserted in the expression vector into a target cell (host cell) and expressing it in the cell. The expression vector generally contains a promoter sequence necessary for expression of a nucleic acid inserted, an enhancer sequence for promoting expression, and the like. An expression vector containing a selective marker can also be used. When such an expression vector is used, presence or absence (and its degree) of introduction of the expression vector can be confirmed using a selective marker.

Insertion of the nucleic acid of the present invention into the vector, insertion of a selective marker gene (if necessary), insertion of a promoter (if necessary), and the like can be performed in a standard recombinant DNA technique (for example, a known method of using a restriction enzyme and a DNA ligase, which can be referred in Molecular Cloning, Third Edition, 1.84, Cold Spring Harbor Laboratory Press, New York).

As host cells, there can be employed, for example, microbial cells of koji mold (for example, *Aspergillus oryzae*), bacilli (for example, *Bacillus subtilis*), *Escherichia coli*, and *Saccharomyces cerevisiae*, in terms of easy handling; however, any host cell in which a recombinant DNA can be replicated and a gene encoding a modified enzyme can be expressed can be utilized. Preferably, *Escherichia coli* and *Saccharomyces cerevisiae* can be employed as a host organism. *Candida* yeasts such as *Candida cylindracea* can also be used as a host organism. In addition, *Pichia* yeasts such as *Pichia pastoris* can also be used as a host organism. Strains of *Escherichia coli* can be *Escherichia coli* strain BL21(DE3)pLysS in cases of using a T7-based promoter, and *Escherichia coli* strain JM109 in other cases. Strains of *Saccharomyces cerevisiae* can be *Saccharomyces cerevisiae* strain SHY2, AH22, or INVSc1 (Invitrogen).

Another aspect of the present invention relates to a microorganism having the recombinant DNA of the invention (that is, a transformant). The microorganism of the invention can be obtained by transfection or transformation using the vector of the invention described above. The transfection or transformation can be performed in, for example, the calcium chloride method (J. Mol. Biol., 53, 159 (1970)), the Hanahan method (J. Mol. Biol., 166, 557 (1983)), the SEM method (Gene, 96, 23 (1990)), a method by Chung, et al. (Proc. Natl. Acad. Sci. U.S.A. 86, 2172 (1989)), the calcium phosphate coprecipitation method, electroporation (Potter, H. et al., Proc. Natl. Acad. Sci. U.S.A. 81, 7161-7165 (1984)), and lipofectin (Felgner, P. L. et al., Proc. Natl. Acad. Sci. U.S.A. 84, 7413-7417 (1984)). The microorganism of the present invention can be used for producing the modified enzyme of the invention.

3. Enzyme Preparation Containing Modified Lipase

The modified enzyme of the present invention is provided, for example, in the form of an enzyme preparation. The enzyme preparation may contain an excipient, a buffer agent, a suspending agent, a stabilizer, a preservative, an antiseptic, saline and the like besides the active ingredient (the modified enzyme of the present invention). As the excipient, starch, dextrin, maltose, trehalose, lactose, D-glucose, sorbitol, D-mannitol, white soft sugar, glycerol and the like can be used. As the buffer agent, phosphates, citrates, acetates and the like can be used. As the stabilizer, propylene glycol, ascorbic acid and the like can be used. As the preservative, phenol, benzalkonium chloride, benzyl alcohol, chlorobutanol, methylparaben and the like can be used.

As the antiseptic, ethanol, benzalkonium chloride, paraoxybenzoic acid, chlorobutanol and the like can be used.

4. Uses of Modified Lipases

A further aspect of the present invention relates to uses of modified enzymes and enzyme preparations according to the present invention, thereby providing different types of reaction (hydrolysis, synthesis, transformation) using the modified enzymes or enzyme preparations. Specifically, modified enzymes or enzyme preparations according to the present invention can be used, for example, for the degradation of fats and oils contained in fat-and-oil-containing wastewater and within grease traps, food processing (for example, production of milk flavor, degradation of fats and oils, production of FPA/DHA, bread making, egg white treatment), and organic synthesis reactions (for example, optical resolution of racemates, asymmetrization of symmetric compounds, regioselective acylation of hydroxyl groups). The modified enzymes according to the present invention have excellent reactivity and stability at a high temperature. These properties enhance the reactivity especially toward fats and oils that solidify at room temperature (such as oils and fats containing saturated fatty acids, and animal fats), and allow the modified enzymes to work advantageously in applications as described above. There is now described, as a specific example of these applications, a method for degradation of fats and oils in wastewater and the like, in which it is desired that the reaction with the lipase is carried out at a high temperature. Fats and oils present in wastewater and within grease straps often contain those that have high melting/freezing points and are thus difficult to be hydrolyzed by the lipase at room temperature (20° C.±10° C.), for example, animal fats and oils such as lard and tallow. The method for degradation of fats and oils according to the present invention is useful for efficient degradation of such fats and oils. Therefore, as a preferred embodiment, the method for degradation of fats and oils according to the present invention is intended to degrade a material containing fats and oils with high melting/freezing points, which may be referred to hereinafter as a fat/oil containing material. Examples of the fat/oil containing material include wastewater from restaurants and eating places, hospitals, hotels, and the like; household wastewater; industrial wastewater discharged from food-processing and fat/oil-processing plants, and the like; and wastewater and deposits within grease traps placed at kitchens, and the like. The "grease trap" is a device for separating and collecting oils in wastewater, and typically includes three compartments. The first compartment is equipped with a basket to capture pieces of foodstuffs, garbage, and others. The second compartment is for separating the oils from the water. The wastewater from which the oils have been separated is sent to the third compartment to remove sedimentary debris and others. Grease traps are compulsorily required to be placed at kitchens for business use in restaurants and eating places, hospitals, hotels, and the like.

In the method for degradation of fats and oils according to the present invention, a modified enzyme according to the present invention is allowed to act on a fat/oil containing material as described above. For example, a modified enzyme or enzyme preparation according to the present invention is added to a solution including a fat/oil containing material to form a state where the modified enzyme and the fat/oil-containing material are in contact with each other, thereby to perform an enzyme reaction. In order to take advantage of characteristics of the present invention and at the same time, achieve efficient hydrolysis, the enzyme reaction is preferably carried out at a high temperature.

Here, the high temperature refers to 30° C. to 70° C., preferably 40° C. to 65° C., further preferably 45° C. to 60° C. The reaction time can be set so as to obtain a desired rate of degradation, taking into consideration the type and amount of the fat/oil containing material to be treated, the amount of the enzyme used, and others. The reaction time is, by way of example, from 1 hour to 2 days.

5. Methods for Preparation of Modified Lipases

A further aspect of the present invention relates to a method for preparing a modified enzyme according to the present invention. In an embodiment of the method for preparation according to the present invention, modified enzymes that have been successfully obtained by the present inventors are prepared by genetic engineering procedures. In this embodiment, a nucleic acid encoding the amino acid sequence represented by any of SEQ ID NOs: 2 to 7 is prepared (step (I)). Here, a "nucleic acid encoding a particular amino acid sequence" gives, upon its expression, a polypeptide having the amino acid sequence encoded thereby, and includes not only a nucleic acid consisting of a base sequence corresponding to the amino acid sequence, but also a nucleic acid that may have an additional sequence added thereto, which may or may not encode an amino acid sequence. The degeneracy of codons is also taken into consideration. A "nucleic acid encoding the amino acid sequence represented by any of SEQ ID NOs: 2 to 7" can be prepared in an isolated state, for example, by standard genetic engineering, molecular biological, and biochemical procedures, with reference to the sequence information disclosed in the specification and accompanying sequence listing. As mentioned above, any of the amino acid sequences represented by SEQ ID NOs: 2 to 7 results from a particular mutation of the amino acid sequence of the *Candida cylindracea*-derived lipase. Therefore, a nucleic acid (gene) encoding the amino acid sequence represented by any of SEQ ID NOs: 2 to 7 can also be obtained by applying a required mutation to the gene encoding the *Candida cylindracea*-derived lipase. A large number of methods for site-specific base sequence substitution are known in the art (see, for example, Molecular Cloning, Third Edition, Cold Spring Harbor Laboratory Press, New York), and from among these, suitable methods can be selected and used. As a site-specific mutagenesis method, site-specific saturation mutagenesis of amino acids can be employed. The site-specific saturation mutagenesis of amino acids is a "Semi-rational, semi-random" method in which the position involved in the desired function of a given protein is estimated on the basis of the three-dimensional structure of the protein, which is then subjected to amino acid saturation mutagenesis (J. Mol. Biol. 331, 585-592 (2003)). For example, site-specific saturation mutagenesis of amino acids can be performed by using kits, such as Quick change (Stratagene), and overlap extension PCR (Nucleic Acid Res. 16, 7351-7367 (1988)). As the DNA polymerase for use in the PCR, for example, Taq polymerase can be employed. Preferably, use is made of high-accuracy DNA polymerases such as KOD-PLUS-(Toyobo Co., Ltd.) and Pfu turbo (Stratagene).

Following the step (I), the prepared nucleic acid is expressed (step (II)). For example, firstly, an expression vector inserted with the above described nucleic acid is prepared and a host cell is transformed using this constructed vector.

Then, a transformant is cultured under the condition of producing a modified enzyme that is an expressed product. Culture of the transformant may follow a general method. An assimilable carbon compound may be used as a carbon source used for a medium, and examples such as glucose, sucrose, lactose, maltose, molasses, and pyruvic acid are used. An available nitrogen compound may be used as a nitrogen source, and examples such as peptone, meat extract, yeast extract, casein hydrolysate, and soybean bran alkali extract are used. Other than those substances, phosphate, carbonate, sulfate, salts of magnesium, calcium, potassium, iron, manganese and zinc, specific amino acids, specific vitamins, and the like are used according to necessity.

On the other hand, a culture temperature can be set within the range from 30 to 40° C. (preferably at around 37° C.). A culture time can be set by considering growing characteristics of a transformant to be cultured and production characteristics of a modified enzyme. A pH of a medium is set within the range wherein a transformant grows and an enzyme is produced. The pH of a medium is preferably set at about 6.0 to 9.0 (preferably at around pH 7.0).

Subsequently, the expressed product (modified enzyme) is collected (step (III)). A culture liquid containing fungus bodies after culture may be used as an enzyme solution directly or after undergoing condensation, removal of impurities, or the like, but the expressed product is generally once collected from the culture liquid or fungus bodies. When the expressed product is a secretion type protein, it can be collected from the culture liquid, and in other cases, the expressed product can be collected from cells. In the case of collecting from the culture liquid, for example, an undissolved substance is removed by filtration and centrifugation on a culture supernatant, and then, a purified product of a modified enzyme can be obtained by separation and purification in combination of vacuum concentration, membrane concentration, salting out using ammonium sulfate or sodium sulfate, fractional precipitation by methanol, ethanol, or acetone, dialysis, heating treatment, isoelectric treatment, various kinds of chromatography such as gel filtration, adsorption chromatography, ion exchange chromatography, and affinity chromatography (for example, gel filtration with Sephadex gel (GE Healthcare Life Sciences), etc., DEAE sepharose CL-6B (GE Healthcare Life Sciences), octyl sepharose CL-6B (GE Healthcare Life Sciences), CM sepharose CL-6B (GE Healthcare Life Sciences)). On the other hand, in the case of collecting the expressed product from cells, a culture liquid is subjected to filtration, centrifugation, or the like, to thus obtain the cells, then the cells are crushed by a mechanical method such as a pressure treatment and an ultrasonic treatment, or an enzymatic method with a lysozyme or the like, thereafter carrying out separation and purification in the same manner as described above, and a purified product of a modified enzyme can be thus obtained.

The purified enzyme obtained as described above can be provided after being powdered, for example, by freeze dry, vacuum dry, or spray dry. In this time, the purified enzyme may be previously dissolved in a phosphoric acid buffer solution, a triethanol amine buffer solution, a tris-hydrochloric acid buffer solution, or a GOOD buffer solution. Preferably, a phosphoric acid buffer solution and a triethanol amine buffer solution can be used. Note that, for the GOOD buffer solution herein, PIPES, MES or MOPS is exemplified.

Generally, genetic expression and collection of the expressed product (modified enzyme) are carried our using an appropriate host-vector system as described above, but a cell-free synthesis system may also be employed. Herein, the "cell-free synthesis system (cell-free transcription system, cell-free transcription/translation system)" refers to in vitro synthesis of mRNA or a protein from a nucleic acid (DNA or mRNA) being a template, which codes for the mRNA or the protein, using a ribosome, a transcription/translation factor derived from living cells (alternately, obtained in a genetic engineering technique) or the like, not using living cells. In the cell-free synthesis system, a cell extraction obtained from a cell disruptor that is purified according to necessity is generally used. The cell extraction generally includes ribosome necessary for protein synthesis and various factors such as an initiation factor, and various enzymes such as tRNA. When a protein is synthesized, this cell extraction is added with other substances necessary for protein synthesis, such as various amino acids, energy sources (e.g., ATP and GTP), and creatine phosphate. As a matter of course, ribosome and various factors and/or various enzymes, and the like, which are separately prepared, may be supplemented if necessary in the protein synthesis.

Development of a transcription/translation system reconstructing various molecules (factors) necessary for protein synthesis has also been reported (Shimizu, Y. et al.: Nature Biotech., 19, 751-755, 2001). In this synthesis system, a gene of 31 kinds of factors composed of 3 kinds of initiation factors constituting a protein synthesis system of bacteria, 3 kinds of elongation factors, 4 kinds of factors associated with termination, 20 kinds of aminoacyl tRNA synthesis enzymes that make each amino acid combine with tRNA, and a methionyl tRNA formyl transfer enzyme is amplified from an *Escherichia coli* genome, and a protein synthesis system is reconstructed in vitro using them. Such a reconstructed synthesis system may be used in the present invention.

The term "cell-free transcription/translation system" is interchangeably used with a cell-free protein synthesis system, an in vitro translation system or an in vitro transcription/translation system. In the in vitro translation system, RNA is used as a template to synthesize a protein. Any of RNA, mRNA, an in vitro transcribed product, or the like is used as the template RNA. On the other hand, in the in vitro transcription/translation system, DNA is used as a template. The template DNA should include in a ribosome bonding region, and preferably contains a suitable terminator sequence. In addition, in the in vitro transcription/translation system, a condition of adding factors necessary for each reaction is established so that a transcription reaction and a translation reaction proceed sequentially.

EXAMPLES

<Searching for Mutation Points Effective for Improving Reactivity or Stability at High Temperature>

With the aim of improving high-temperature reactivity or stability of *Candida cylindracea*-derived lipase (SEQ ID NO: 1), mutation points (amino acid residues for which substitution was to be made) were selected from the viewpoints of formation of disulfide bonds, loop stabilization (Pro introduction), enhancement of hydrogen bonding, and enhancement of hydrophobicity, whereby 22 variants (modified lipases) were designed. The respective variants designed were produced by the method described below, and evaluated for their properties. Here, the amino acid sequence represented by SEQ ID NO: 1 represents the mature form (without signal peptide) of *Candida cylindracea*-derived lipase; the amino acid sequence comprising the signal peptide sequence thereof, and the gene sequence encoding it are set forth in SEQ ID NOs: 22 and 23, respectively.

(1) Obtaining of DNA Sequences Encoding Mutated Amino Acid Sequences

A *Pichia pastoris* host expression system (*Pichia* Expression Kit, available from Invitrogen) was used. As a plasmid, use was made of pPIC3.5K. The gene of *Candida cylindracea*-derived LIP1 as a template was codon-optimized for use in budding yeast (*Saccharomyces cerevisiae*). Mutations were made by an inverse PCR method (using Takara Bio Primestar mutagenesis kit), thereby to prepare genes encoding variants with amino acid substitutions at the selected mutation points (SEQ ID NOs: 14 to 19). A plasmid containing a variant of the LIP1 gene was transformed into *E. coli* DH5α. Subsequently, the plasmid was extracted from the transformed *E. coli* cells.

(2) Transformation of *Pichia pastoris* and Preparation of Enzyme Solutions

The plasmid containing the variant of the LIP1 gene was transformed into *Pichia pastoris* GS115 (using *Pichia* Expression Kit, available from Invitrogen). *Pichia pastoris* transformants obtained were cultured, and the cultured supernatants were collected. The culturing can be performed by the method described in the instruction manual of the kit. For example, a *Pichia pastoris* transformant was inoculated in BMGY medium (2.0% Peptone; 1.0% Yeast extract; 100 mM Potassium phosphate, pH 6.0; 1.34% Yeast Nitrogen Base (without Amino Acids); 0.4 µg/mL Biotin; 1.0% Glycerol) and cultured with shaking in a test tube at 30° C. for 2 days. Then, the cultured solution was inoculated into a baffled flask containing 50 mL of BMMY medium (2.0% Peptone; 1.0% Yeast extract; 100 mM Potassium phosphate, pH 6.0; 1.34% Yeast Nitrogen Base (without Amino Acids); 0.4 µg/mL Biotin; 0.5% Methanol) and incubated at 30° C., at 200 rpm for 1 day. The cells were harvested, and then suspended in 50 mL of BMMY medium and subjected to culturing in a baffled flask under the same conditions. Methanol was added about every 12 hours to a final concentration of 0.5% for the induction of enzyme expression for 4 days. For the respective transformants, the cultured supernatant (crude enzyme solution) was collected and evaluated for their properties, i.e., high-temperature reactivity and stability, of the variant enzyme. By comparison with the wild-type enzyme, eight variants were selected that were found to have improvements in these properties.

(3) Purification of Variants (Modified Lipases)

For the selected variants, the cultured supernatant was desalted and concentrated, and replaced into 20 mM McIlvaine buffer (pH 3.8). The solution after the replacement was applied to a column of SP-sepharose (GE healthcare) equilibrated with the same buffer. The column was eluted with a linear gradient of 0 to 0.5 mol/L NaCl, and fractions with lipase activity were collected to obtain a purified enzyme.

(4) Evaluation of High-Temperature Reactivity

Each of the purified enzymes was measured for enzyme activity at 30° C. and at 60° C. with the lipase kit S (DS Biopharma Medical Co., Ltd.) to ascertain whether the enzyme had improved reactivity at the high temperature. The high-temperature reactivity of the enzyme was evaluated in terms of the relative activity thereof, which is a ratio of enzyme activity at 60° C. to that at 30° C., calculated by the following formula.

Relative activity=(enzyme activity at 60° C./enzyme activity at 30° C.)×100(%)

The evaluation results are shown in FIG. 1. Six variants were observed to have improvements in the reactivity at the high temperature. Variants 1 (T130C-S153C) and 5 (S283Y) have particularly high reactivity at the high temperature.

(5) Evaluation of High-Temperature Stability

Each of the purified enzyme solutions was diluted with phosphate buffer (pH 6.0) so that the absorbance (A280) of the resulting enzyme solution at 280 nm was equal. The diluted solution was heated at 50° C. for 30 minutes, and then cooled on ice, followed by centrifugation. For the respective samples, the enzyme activity of the centrifuged supernatant was measured with the lipase kit S (DS Biopharma Medical Co., Ltd.). The residual activity percent of the enzyme was calculated as described below, from this measurement result, that is, the enzyme activity after heat treatment, and that before heat treatment, to evaluate the high-temperature stability thereof.

Residual activity percent=(enzyme activity after heat treatment/enzyme activity before heat treatment)×100(%)

Figure 2:
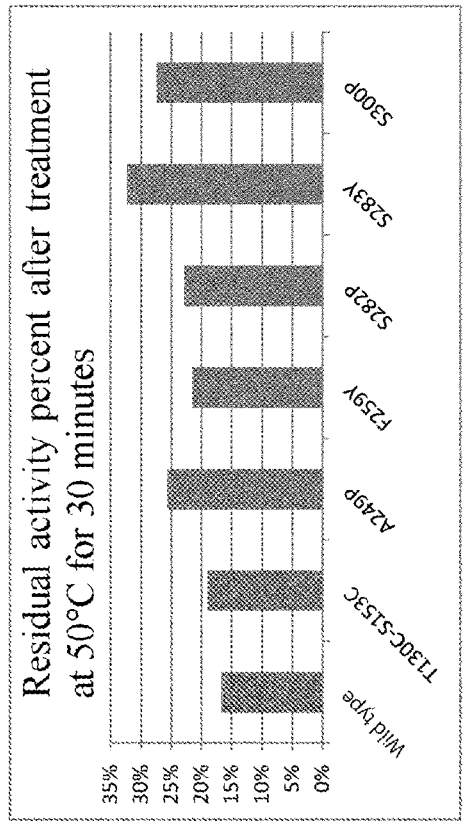
FIG. 2 The stability of variants at a specified high temperature. Residual activity percents of the variants after treatment at 50° C. for 30 minutes were compared with that of the wild-type enzyme.

The evaluation results are shown in FIG. 2. Six variants were observed to have improvements in the stability at the high temperature. Variants 2 (A249P), 5 (S283Y), and 6 (S300P) have particularly high stability at the high temperature.

As described above, 6 variants having excellent reactivity or stability at the high temperature were successfully obtained. The amino acid sequences of these variants are shown below.

Variant 1 (T130C-S153C): SEQ ID NO: 2
Variant 2 (A249P): SEQ ID NO: 3
Variant 3 (F259Y): SEQ ID NO: 4
Variant 4 (S282P): SEQ ID NO: 5
Variant 5 (S283Y): SEQ ID NO: 6
Variant 6 (S300P): SEQ ID NO: 7

INDUSTRIAL APPLICABILITY

The modified lipases of the present invention have excellent reactivity or stability at a high temperature. Therefore, the modified lipases are of high utility value in various applications in which enzyme reactions at a high temperature are desired.

The present invention is not limited to the description of the embodiments and working examples of the above-described invention in any way. The present invention includes various modifications that can be easily arrived at by a person skilled in the art without departing from the scope of the description of the claims. The contents of the articles, published patent publications, patent publications, and the like explicitly specified in the present specification shall be cited by incorporating the entire contents thereof.

---

The invention claimed is:

1. A modified lipase with improved reactivity and/or stability at a high temperature, as compared to a lipase consisting of the amino acid sequence of SEQ ID NO: 1, the modified lipase having the amino acid sequence of SEQ ID NO: 1 except as having one or more amino acid substitutions selected from the group consisting of T130C-S153C, A249P, F259Y, S282P, S283Y, and S300P,
   or alternatively the modified lipase having an amino acid sequence having 92% or more sequence identity with the amino acid sequence of SEQ ID NO: 1 with one or more amino acid substitutions selected from the group consisting of T130C-S153C, A249P, F259Y, S282P, S283Y, and S300P, with the proviso that the amino acid sequence of the modified lipase is different from the amino acid sequence of SEQ ID NO: 1 at a position or positions other than the position(s) at which the amino acid substitution(s) is(are) made;
   wherein the high temperature is a temperature above 40 Celsius degree.

2. The modified lipase according to claim 1, wherein the amino acid substitution contained in the amino acid sequence of the modified lipase is T130C-S153C or S283Y, and the modified lipase has improved reactivity at a high temperature.

3. The modified lipase according to claim 1, wherein the amino acid substitution contained in the amino acid sequence of the modified lipase is A249P, S283Y, or S300P, and the modified lipase has improved stability at a high temperature.

4. A lipase with improved reactivity and/or stability at a high temperature, as compared to a lipase consisting of the amino acid sequence of SEQ ID NO: 1, comprising the amino acid sequence of any of SEQ ID NOs: 2 to 7, or an amino acid sequence having 92% or more sequence identity with the amino acid sequence of any of SEQ ID Nos: 2 to 7, with the proviso that the amino acid sequence is different at a position or positions other than those corresponding to cysteine at positions 130 and 153 in the amino acid sequence of SEQ ID NO: 2, proline at position 249 in the amino acid sequence of SEQ ID NO: 3, tyrosine at position 259 in the amino acid sequence of SEQ ID NO: 4, proline at position 282 in the amino acid sequence of SEQ ID NO: 5, tyrosine at position 283 in the amino acid sequence of SEQ ID NO: 6, and proline at position 300 in the amino acid sequence of SEQ ID NO: 7, when the respective amino acid sequences are used as a reference sequence to determine the sequence identity;
   wherein the high temperature is a temperature above 40 Celsius degree.

5. A gene encoding the modified lipase according to claim 1.

6. The gene according to claim 5, comprising a base sequence of any of SEQ ID NOs: 8 to 19.

7. A recombinant DNA containing the gene according to claim 5.

8. A microorganism carrying the recombinant DNA according to claim 7.

9. The microorganism according to claim 8, wherein the host is *Escherichia coli*, *Candida cylindracea*, *Aspergillus oryzae*, *Bacillus subtilis*, or *Pichia pastoris*.

10. An enzyme preparation comprising the modified lipase according to claim 1.

11. A method for degradation of fats and oils comprising allowing the modified lipase according to claim 1 or an enzyme preparation comprising the modified lipase according to claim 1 to act on the fats and oils to carry out an enzyme reaction.

12. The method for degradation according to claim 11, wherein the enzyme reaction is carried out at 30° C. to 70° C.

13. A modified lipase with improved reactivity and/or stability at a high temperature, as compared to a lipase consisting of the amino acid sequence of SEQ ID NO: 1, the modified lipase having the amino acid sequence of SEQ ID NO: 1 except as having the amino acid substitutions is T130C-S153C,
   or alternatively the modified lipase having an amino acid sequence having 90% or more sequence identity with the amino acid sequence of SEQ ID NO: 1 with one or more amino acid substitutions of T130C-S153C, with the proviso that the amino acid sequence of the modified lipase is different from the amino acid sequence of SEQ ID NO: 1 at a position or positions other than the position(s) at which the amino acid substitution is made;

wherein the high temperature is a temperature above 40 Celsius degree.

\* \* \* \* \*